United States Patent
Manneck et al.

(10) Patent No.: US 10,596,097 B2
(45) Date of Patent: Mar. 24, 2020

(54) METHOD FOR MULTI-TONAL COLOR MODIFICATION OF KERATINOUS FIBERS

(71) Applicant: Henkel AG & Co. KGaA, Duesseldorf (DE)

(72) Inventors: Hartmut Manneck, Barnitz (DE); Stefan Hoepfner, Hamburg (DE); Matthias Schweinsberg, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/064,370

(22) PCT Filed: Dec. 1, 2016

(86) PCT No.: PCT/EP2016/079382
§ 371 (c)(1),
(2) Date: Jun. 20, 2018

(87) PCT Pub. No.: WO2017/108364
PCT Pub. Date: Jun. 29, 2017

(65) Prior Publication Data
US 2019/0021980 A1   Jan. 24, 2019

(30) Foreign Application Priority Data

Dec. 21, 2015   (DE) .................. 10 2015 226 171

(51) Int. Cl.
*A61Q 5/10* (2006.01)
*A61K 8/73* (2006.01)
*A61Q 5/08* (2006.01)

(52) U.S. Cl.
CPC ............... *A61K 8/737* (2013.01); *A61K 8/73* (2013.01); *A61K 8/732* (2013.01); *A61K 8/733* (2013.01); *A61Q 5/08* (2013.01); *A61Q 5/10* (2013.01); *A61K 2800/4324* (2013.01); *A61K 2800/882* (2013.01)

(58) Field of Classification Search
CPC ... A61Q 5/10; A61Q 5/08; A61K 8/22; A61K 8/73; A61K 2800/884; A61K 2800/882; A61K 8/042
See application file for complete search history.

(56) References Cited

U.S. PATENT DOCUMENTS

| | | | |
|---|---|---|---|
| 2008/0083420 A1* | 4/2008 | Glenn | A45D 19/0008 132/208 |
| 2008/0087293 A1* | 4/2008 | Glenn | A45D 19/0008 132/210 |

FOREIGN PATENT DOCUMENTS

| | | |
|---|---|---|
| DE | 19756454 C1 | 6/1999 |
| EP | 2574331 A2 | 4/2013 |
| WO | 2007087978 A1 | 8/2007 |
| WO | 2014164213 A1 | 10/2014 |
| WO | 2014187575 A1 | 11/2014 |
| WO | 2015028015 A1 | 3/2015 |

OTHER PUBLICATIONS

EPO, International Search Report and Written Opinion issued in International Application No. PCT/EP2016/079382, dated Mar. 22, 2017.

* cited by examiner

*Primary Examiner* — Eisa B Elhilo
(74) *Attorney, Agent, or Firm* — Lorenz & Kopf, LLP

(57) ABSTRACT

The subject matter of the present disclosure is a method for treatment keratinous fibers which make it possible to color the hair in a single treatment session and simultaneously achieve a multi-tonal coloring with sections (strands) having different colors, more particularly lighter ("highlights") sections (strands), wherein the use of solid, flat separating aids, more particularly foils from solid materials such as aluminum, paper or Styrofoam and similar materials is not required.

20 Claims, No Drawings

METHOD FOR MULTI-TONAL COLOR MODIFICATION OF KERATINOUS FIBERS

CROSS-REFERENCE TO RELATED APPLICATION

This application is a U.S. National-Stage entry under 35 U.S.C. § 371 based on International Application No PCT/EP2016/079382, filed Dec. 1, 2016 which was published under PCT Article 21(2) and which claims priority to German Application No. 10 2015 226 171.9, filed Dec. 21, 2015, which are all hereby incorporated in their entirety by reference.

TECHNICAL FIELD

To achieve permanent, intense coloring of keratinous fibers, particularly human hair, with corresponding fastness properties, so-called oxidative coloring agents are used. Such coloring agents usually include oxidative dye precursors, so-called developer components and coupler components which react with each other, particularly oligomerize, under the influence of oxidants or atmospheric oxygen and thus develop the actual dyes. The oxidizing coloring agents are exemplified by outstanding, long-lasting color results. For temporary colors, dyes or tints including so-called partially-oxidizing agents are normally used as the coloring component.

BACKGROUND

In addition to dyeing, the lightening of one's own hair color and/or bleaching is a very specific preference of many consumers, because a blond hair color is considered attractive and desirable from a fashion perspective. If substrates are to be lightened or even bleached, the substrate-dyeing dyes, the hair's natural melanin, for example, are typically decolorized oxidatively using appropriate oxidants, such as hydrogen peroxide.

When hair is bleached—more particularly when hair is bleached at home by consumers themselves—the problem is that natural tints become completely covered, making multi-tone hair bleaching difficult to realize.

In order to lend the hair a natural appearance, partially decolorizing both non-dyed and already dyed hair by the targeted application of oxidants is known from the prior art. The hair sections ("strands") to which the oxidant is applied typically bleach in portions, the result being a multi-tone hair color. Dyeing individual hair sections ("strands") with a different color is also known from the prior art. The oxidant, possibly including dye, is applied to the hair by employing a brush or similar tool, wherein the hair that is to remain untreated is protected against contact with the oxidant, possibly including dye, by employing solid, flat separating mechanisms or apparatuses, more particularly with soils from solid materials, such as aluminum, paper or Styrofoam and similar materials, or by employing a so-called "highlighting cap". Such a highlighting cap is disclosed in WO 2007/087978, for instance.

This type of application addresses the problem of the most natural possible coloring of hair, but only enables coloring with "highlights". For "lowlights", i.e. darker portions, a subsequent coloring must take place. The cases describe above, therefore, a time-consuming second decolorization or coloration step would be necessary after the first coloring. Therefore, for home use, in particular, the entire hair would have to be colored before the user can add "highlights" or "lowlights". Many consumers find this to be too time-consuming and frustrating, because the essential color-changing step took place at the beginning and is only "corrected" in a second step.

With the prior art highlighting method, the foils or the highlighting cap accumulate at the end of the method as solid waste, which must be discarded This causes an environmental load. Handling the foils is difficult in part; for example, access to as yet untreated hair is obstructed by foils already in place. Moreover, foils made of paper, plastic and Styrofoam can adhere to the treated hair poorly and slip out.

Certain foil types and applications can involve overheating, because the possibility of dissipating the reaction heat of the exothermic oxidation process by evaporating volatile formula constituents, such as water for example, is severely restricted by the steam-impermeable foils.

Production of commercial hair coloring agents, like the production of other products, is subject to high cost pressure. Therefore, the person skilled in the art strives to harmonize as many recipe components as possible. With coloring creams, for example, a specific emulsion base is used as a "carrier". Any additives which provide an individualized product benefit—whether dye powder mixtures for a specific nuance or select nourishing agents to treat different hair qualities in an optimal manner—must be as compatible as possible with the carrier, e.g. the coloring cream base. In the process, the so-called color shift is a criterion for compatibility. With the addition of custom additives, color differences can occur between the hair color achieved with the additive-free (standard) carrier and the hair color achieved with the carrier including additive. Such color differences are described by the present application as "color shift". This color shift, also referred to as dE or $\Delta E$, can be determined by colorimetry by employing a colorimeter, which measures the colors in the $L^*,a^*,b^*$ color space by employing a colorimeter from Datacolor, Type Spectraflash 450, for example.

The $L^*,a^*,b^*$ color space means the CIELAB color space. The L-value denotes the lightness of the color (black-white axis); the higher the value for L, the lighter the color. The a-value denotes the red-green axis of the system; the higher this value, the more the color is shifted into the red. The b-value denotes the yellow-blue axis of the system; the higher this value, the more the color is shifted into the yellow.

The color shift $\Delta E$, i.e. the color difference between two (hair) colors, for which a $L^*,a^*,b^*$ value combination was determined in each case, is calculated according to the following formula:

$$\Delta E=(\Delta L^2+\Delta a^2+\Delta b^2)^{0.5}$$

The greater the value for $\Delta E$, the more pronounced the color difference or "color shift". Color differences with an $\Delta E<1$ are not perceptible to the human eye. Color differences with an $\Delta E<2$ are visible to the trained eye. Color differences with an $\Delta E>2$ are visible even to the untrained eye.

In the worst case, the addition of an additive to a coloring agent carrier causes a color shift, compared to the carrier without additives (standard) with $\Delta E>2$, which is visible to even the consumer's untrained eye. To avoid extensive tests with respect to the achievable hair coloration and, where applicable, the fastness properties having to be carried out with every additive change of the standard carrier, it is therefore desirable to identify active ingredients and nourishing agents for the hair, the addition of which causes no or at least only a minimal color shift.

Patent applications EP2574331A2 and WO2014164213A1 disclose coloring methods that permit multi-tone coloring in one coloring step, wherein a thickening agent, more particularly an anionic or cationic associative polymer (EP2574331A2) having a thickening effect is added to a hair coloring agent in higher concentrations before application to selected hair sections or strands. The coloring agent thickens on the hair strands to form a highly-viscous paste, thereby achieving a separating effect to adjacent hair sections or strands. The color exchange between adjacent strands, which were treated with various coloring or bleaching agents, is thus minimized. Over the total coloring agent application time of approx. 30 to 60 minutes, the dye diffusion between adjacent strands, which are in physical contact with one another, cannot however be completely avoided. The corresponding commercial product for professional salon use is therefore marketed with the instruction that the color difference between adjacent strands should not be more than about 3 color tones. Otherwise, the color result would be impaired by a visible color exchange.

BRIEF SUMMARY

This disclosure provides a method for color-changing keratinous fibers. The method includes the steps of a. preparing a coloring or lightening composition (A) including a)i. at least one alkalizing agent, a)ii. optionally at least one consistency enhancer, and a)iii. optionally at least one solvent selected from water and also at least one organic solvent selected from one or more monovalent or polyvalent alcohols having from 2 to 9 carbon atoms, polyethylene glycols having from 2 to 20 ethylene glycol units, as well as mixtures of the solvents. The lightening composition (A) also optionally includes a)iv. at least one oxidation dye precursor and/or at least one partially-oxidizing hair dye. Moreover, a)v. wherein the coloring or lightening composition (A), insofar as, relative to its weight, includes more than about 7 wt. % water, it has a pH value of from about 6.0 to about 11.5, measured at about 20° C. Also, insofar as the composition (A), relative to its weight, includes from about 0 to about 7 wt. % water, it is an about 30 wt. % dispersion in water and has a pH value of from about 6.0 to about 12.0, measured at about 20° C. The method also includes the step of b. preparing an oxidant composition (B), including b)i. from about 1 to about 18 wt. % hydrogen peroxide, relative to the weight of the composition (B), and b)ii. water, b)iii. wherein the oxidant composition (B) has a pH value from about 2.5 to about 6.5. The method also includes the step of c. preparing a gelling composition (C) including c)i. from about 0.1 to about 3 wt. %, relative to the weight of the composition (C), at least one salt of a multivalent metal ion, selected from calcium-, strontium-, barium- and aluminum salts having a water solubility at about 20° C. of at least about 500 mg/l. If the polysaccharide, which forms a gel with calcium ions, includes kappa carragheenan or a salt thereof, the gelling composition (C) includes from about 0.1 to about 3 wt. %, relative to the weight of the composition (C), at least one salt, selected from potassium, calcium-, strontium-, barium- and aluminums salts having a water solubility at about 20° C. of at least about 500 mg/l. Moreover, the gelling composition (C) includes c)ii. from about 50 to about 99 wt. %, relative to the weight of the composition (C), water, and c)iii optionally at least one cation polymer selected from cationized guar ethers, c)iv. wherein the gelling composition (C) has a pH value from about 4 to about 12, measured at about 20° C. Moreover, the gelling composition (C) is optionally produced in-situ or from about 0.01 to about 24 hours before the instant method is applied, by mixing a solid, gelling composition (C'), including the at least one salt c)i in powder form and optionally at least one cation polymer, which is selected from cationized guar ethers, in powder form, with water c) iii, then, from about 1 to about 600 seconds thereafter, d. producing a mixture (M) of (A) and (B), having a pH value of from about 6.0 to about 11, measured at about 20° C.; after from about 1 to about 600 seconds. The method also includes the steps of e. applying at least one partial quantity of (M) on at least one keratin fiber section to be colored and/or lightened; from about 1 to about 600 seconds thereafter f applying the gelling composition (C) on the keratinous fiber section(s) treated with (M); g. repeating steps e. and f as many times as desired, and h. leaving the gelling composition (C) on the keratinous fibers for a time of from about 0.1 to about 60 minutes, and then rinsing the keratinous fibers with water and, if required, with a cleaning agent, post-treating the fibers with a conditioning agent and then drying, if required. Moreover, the method includes the application of at least one polysaccharide which can form a gel with calcium ions in a hydrous medium, and which is selected from alginic acid, kappa carragheenan, iota carragheenan and pectin, as well as at least one salt of the aforementioned polysaccharides, selected from the alkali metal-, ammonium-, mono-, di- and trialkyl ammonium-, mono-, di- and trialkanolammonium- and magnesium salts, wherein in the case of salts of the kappa carragheenan, the alkali metal salt thereof is selected from lithium- and sodium salts, wherein these polysaccharides are not included in the gelling composition (C).

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The present disclosure addressed the problem of preparing a method that permits multi-tone coloring in one step. In the process, the coloring of the hair should include the creation of "highlights" or "lowlights" so that a result is directly visible after rinsing out the coloring agent. The present disclosure also addressed the problem of preparing the most resource-efficient multi-tone coloring method possible, which involves no solid foil waste and uses, wherever possible, only materials from sustainable, non-fossil-based raw materials. In addressing this problem, it was particularly important for the foil substitutes to have a high separating force, just like the flat foils. In other words, permitting the cleanest possible separation of the various colored or bleached fiber sections or fiber strands, without any color exchange between the adjacent strands.

The present application also addressed the problem of providing a method for oxidative hair coloring which enables multi-tone coloring in one step, wherein the additives which replace the foils do not cause any or only a minimal color shift.

The present disclosure also addressed the problem of preparing a multi-tone bleaching or lightening method that permits a simplified visual check of the decolorization development or color development.

The subject matter of the present disclosure is a method for treatment keratinous fibers which make it possible to color the hair in a single treatment session and simultaneously achieve a multi-tonal coloring with sections (strands) having different colors, more particularly lighter ("highlights") sections (strands), wherein the use of solid, flat separating aids, more particularly foils from solid materials such as aluminum, paper or Styrofoam and similar materials is not required.

For this purpose, the ready-to-apply coloring or lightening agent, which normally has a strong alkaline pH value, or its individual components are first mixed with a select polysaccharide, the thickening performance of which is less depending on pH value than the thickening performance of, for example, (meth)acrylic acid-, (meth)acrylic acid ester-, (meth)acrylamide- and/or 2-acrylamido-2-methylpropansulfonic polymers. Instead of mixing the ready-to-apply coloring or lightening agent or its individual components with said selected polysaccharide, the ready-to-use coloring or lightening agent can also first be applied to selected keratin fiber sections, more particularly hair sections, or keratin fiber strands, more particularly hair strands, in the usual way and then sprayed or coated with a hydrous solution of said selected polysaccharide. Then the fiber sections or strands treated with polysaccharide are sprayed or coated with a hydrous solution of a selected salt, the cations of which solidify the selected polysaccharide into a film-forming gel. This film, similar to the strand foils of the known method, acts like a separating layer, which allows adjacent fiber sections or strands to be dyed or bleached different colors. This film also acts as an invisible barrier which enables a simple optical check of the development of the bleaching or lightening effect during the reaction.

In principle, the method is also suitable for monotonal color-changing of keratinous fibers. Therefore, the polysaccharide film formation can also be used to retard the undesired drying of the lightening or coloring agent or the release of ammonia during the reaction time on the keratinous fibers. The entire keratin fiber ensemble, e.g. all the main hair, can be treated with the coloring or lightening composition uniformly or in sections, e.g. strand-like, variation of the color tones and highlights, and then subjected to the film-formation procedure.

To the extent required, the expressions "keratinous fibers" and "keratin fibers" are human air, but can also include fur, wool and feathers.

To the extent required, "then" means preferably a period from about 1 to about 600 seconds.

The subject of the present disclosure is a method for multi-tonal color-changing of keratinous fibers comprising the following method steps:

I. preparing a coloring or lightening composition (A), including
a)i. at least one alkalizing agent,
a)ii. optionally at least one consistency enhancer and a)iii. optionally at least one solvent, selected from water and at least one organic solvent, preferably selected from one or more monovalent or polyvalent alcohols having 2 to 9 carbon atoms, polyethylene glycols having 2 to 20 ethylene glycol units, as well as mixtures of said solvents, and
a)iv. optionally at least one oxidation dye precursor and/or at least one partially-oxidizing hair dye,
a)v. wherein the coloring or lightening composition (A), insofar as, relative to its weight, it includes more than about 7 wt. % water, has a pH value in the range of from about 6.0 to about 11.5, measured at about 20° C. and, insofar as the composition (A), relative to its weight, includes from about 0 to about 7 wt. % water, it is an about 30 wt. % dispersion in water has a pH value in the range of from about 6.0 to about 12.0, preferably from about 7.5 to about 11.5, more preferably from about 8 to about 11.0, in each case measured at about 20° C.;

II. preparation of an oxidant composition (B), including
b)i. from about 1 to about 18 wt. % hydrogen peroxide, relative to the weight of the composition (B), and
b)ii. water,
b)iii. wherein the oxidant composition (B) has a pH value in the range from about 2.5 to about 6.5, preferably in the range from about 3 to about 5.5, more particularly in the range from about 3.5 to about 5.0, in each case measured at about 20° C.;

c. preparation of a gelling composition (C), including
d)i. from about 0.1 to about 3 wt. %, preferably from about 0.2 to about 2 wt. %, more preferably from about 0.4 to about 1 wt. %, relative to the weight of the composition (C), at least one salt of a polyvalent metal ion, selected from calcium-, strontium-, barium- and aluminum salts having a water solubility at about 20° C. of at least about 500 mg/l, and also if the polysaccharide, which forms a gel with calcium ions, comprises kappa carragheenan or a salt thereof, the gelling composition (C) including from about 0.1 to about 3 wt. %, preferably from about 0.2 to about 2 wt. %, more preferably from about 0.4 to about 1 wt. %, relative to the weight of the composition (C), at least one salt, selected from potassium, calcium-, strontium-, barium- and aluminums salts having a water solubility at about 20° C. of at least about 500 mg/l,
c)ii. from about 50 to about 99 wt. %, relative to the weight of the composition (C), water,
c)iii. optionally at least one cation polymer, which is preferably selected from cationized guar ethers.
c)iv. wherein the gelling composition (C) has a pH value in the range from about 4 to about 12, preferably in the range of from about 4 to about 6.5, measured at about 20° C.;
the gelling composition (C) optionally being produced in-situ or from about 0.01 to about 24 hours before the color-shift method is applied by mixing a solid, preferably powdery gelling composition (C'), including the at least one salt mentioned under c)i in powder form and optionally at least one cation polymer, which is preferably selected from cationized guar ethers, in powder form, with water c) iii,
then, from about 1 to about 600 seconds thereafter,
d. producing a mixture (M) of (A) and (B), having a pH value in the range of from about 6.0 to about 11, in each case measured at about 20° C.; after from about 1 to about 600 seconds
e. applying at least one partial quantity of (M) on at least one keratin fiber section to be colored and/or lightened;
from about 1 to about 600 seconds thereafter
f. applying, preferably spraying, the gelling composition (C) on the keratinous fiber section(s) treated with (M);
g. repeating steps e. and f as many times as desired,
h. leaving on the keratinous fibers for a time of from about 0.1 to about 60 minutes, preferably from about 1 to about 50 minutes, more preferably from about 10 to about 45 minutes, most preferably from about 30 to about 45 minutes, and then rinsing the keratinous fibers with water and, if required, with a cleaning agent, post-treating the fibers with a conditioning agent and then drying, if required, exemplified in that the method comprises the application of at least one polysaccharide which can form a gel with calcium ions in a hydrous medium, are preferably selected from alginic acid, kappa carragheenan, iota carragheenan and pectin, as well as at least one salt of the aforementioned polysaccharides, selected from the alkali metal-, ammonium-, mono-, di- and trialkyl ammonium-, mono-, di- and trialkanolammonium- and magnesium salts, wherein in the case of salts of the kappa carragheenan, the alkali metal salt thereof is selected only from lithium- and sodium salts, wherein these polysaccharides are not included in the gelling composition (C).

The present disclosure relates to the oxidative color-changing of keratinous fibers, particularly hair. Because when keratinous fibers, more particularly hair, are treated with oxidants, more particularly with hydrogen peroxide, the fiber's natural color/melanin is destroyed to a certain extent, the fibers/hair is inevitably lightened, the color of such fibers/hair changes, even without the presence of oxygen. To the extent required by the present disclosure, therefore, the expression "color change" also comprises lightening and dyeing with one or more dyes.

A person skilled in the art knows various methods for changing the color of human hair. Generally, human hair is dyed using partially-oxidizing dyes or oxidizing dyes, which are produced by oxidatively coupling one or more developer components among one other, or with one or more coupler components. Coupler and developer components are also referred to as oxidizing dye precursors. The colorings achieved with oxidative dyes are typically referred to as permanent or semi-permanent coloring. As oxidants, these agents usually include hydrogen peroxide. Because hydrogen peroxide has inadequate storage stability in the alkaline pH range, oxidative coloring agents typically comprise two components, which are mixed together immediately, i.e. within a period of from about 1 to about 600 seconds, prior to use. The first component, referred to below as "oxidant composition (B)", includes hydrogen in a hydrous solution or emulsion, wherein this composition has an acidic pH value in the range of from about 2.5 to about 6.5, preferably in the range of from about 3 to about 5.5, more preferably in the range of from about 3.5 to about 5.0, in each case measured at about 20° C., in order to stabilize the hydrogen peroxide.

The second component, referred to below as "coloring or lightening composition (A)" includes one or more alkalizing agents in a quantity in which the application mixture of the two components has a pH value in the range of from about 8 to about 11, in each case measured at about 20° C. Insofar as the coloring or lightening composition (A) does not include any dye or only small amounts of partially-oxidizing dyes—the latter serve to cover unwanted color shades that can occur during melanin oxidation—, it is a lightening or bleaching agent. The coloring or lightening composition (A) can also include oxidation dye precursor and/or partially-oxidizing dyes; the resulting application mixture is then used as a coloring agent. In addition, there are also coloring kits and coloring methods wherein the application mixture of the two components has a pH value in the range of approx. 6 to about 7.9; the lightening results of such so-called "acidic" coloring, however, do not achieve the quality achieved with stronger alkaline application mixtures. For the coloring or lightening result, it is important for the ready-to-apply coloring or lightening agent, which is obtained by mixing the coloring or lightening composition (A) with composition (B), to have a pH value in the range of from about 6.5 to about 11.0, preferably from about 8 to about 10.5, more preferably from about 8.5 to about 9.5, in each case measured at about 20° C. At such pH values, the outer keratin fiber layer opens to the optimal extent to absorb the oxidation dye precursor and/or the oxidative effect of the hydrogen peroxide and possibly other peroxide compounds develops to the optimal extent.

Polysaccharide, Selected from Alginic Acid, Kappa Carragheenan, Iota Carragheenan and Pectin, and/or at Least One Salt of Said Polysaccharides An essential component of hair coloring methods preferred as contemplated herein is at least one polysaccharide, which forms a gel with calcium ions in hydrous medium. Polysaccharides preferred as contemplated herein, which can form a gel with calcium ions in a hydrous medium, are preferably selected from alginic acid, kappa carragheenan, iota carragheenan and pectin, as well as at least one salt of the aforementioned polysaccharides, selected from the alkali metal-, ammonium-, mono-, di- and trialkyl ammonium-, mono-, di- and trialkanolammonium- and magnesium salts, wherein in the case of salts of the kappa carragheenan, the alkali metal salt thereof is selected only from lithium- and sodium salts. Hydrous solutions of said polysaccharides and polysaccharide salts demonstrate, depending on concentration, only a slightly increased viscosity, but do not yet form a solid gel.

Alginic acid, sodium alginate, ammonium alginate, magnesium alginate, monoethanolammonium alginate, kappa carragheenan, the lithium salt of kappa carragheenan, the sodium salt of kappa carragheenan, iota carragheenan, the lithium salt of iota carragheenan, the sodium salt of iota carragheenan, the potassium salt of iota carragheenan, the ammonium salt of iota carragheenan, pectin, sodium pectinate, ammonium pectinate, potassium pectinate, as well as mixtures of such substances, are most preferred. Most preferred mixtures as contemplated herein are those from alginic acid and sodium alginate, more particularly mixtures from alginic acid and sodium alginate in the weight ratio of alginic acid to sodium alginate in the range of from about 1:2 to about 2:1, preferably in the range from about 0.8 to about 1.25, most preferably in the weight ratio of about 1:1.

The aforementioned polysaccharides and/or the mentioned salts demonstrate a thickening behavior that is largely independent of pH. However, they gel after the addition of certain polyvalent ions such as calcium, strontium-, barium- and aluminum ions. Moreover, kappa carragheenan also gels when potassium ions are added.

To the extent required by the present disclosure, this behavior is used to produce a foil-like film on selected keratin fiber sections or keratin fiber strands once the coloring or lightening agent has been applied and also prevents, or at least drastically reduces, the exchange with the coloring or lightening agent applied to the adjacent strands. Two embodiments of the method as contemplated herein produce said film.

In the first preferred embodiment of the method, at least one of the aforementioned polysaccharides and/or at least one of the aforementioned salts of polysaccharides is added to one of the compositions (A) or (B) or is included in both compositions (A) and (B) and/or the ready-to-apply coloring or lightening agent mixture of (A) and (B) is mixed together with a third component. Because the aforementioned polysaccharides or their indicated salts to not thicken as heavily in the strong alkaline pH range as, for example (meth)acrylic acid-, (meth)acrylic acid ester-, (meth)acrylamide- and/or 2-acrylamido-2-methylpropansulfonic polymers, which are used in the coloring method according to WO2014164213A1, or ionic associative polymers, which are used in the coloring method according to EP2574331A2, the coloring agent including polysaccharide only has a viscosity in the range of from about 2000 to about 6000 mPas (20° C.) and can thus be distributed easily and evenly on the keratinous fibers. After the keratinous fiber strands have received an adequate application of coloring or lightening agent, a gelling composition is applied, said composition including calcium-, strontium-, barium- and-or aluminum ions or, if the polysaccharide is selected from kappa carragheenan, including potassium ions, calcium-, strontium-barium- and/or aluminum ions in the form of water-soluble salts with a water solubility of at least about 500 mg/l in a hydrous solution. The gelling composition (C) can, for example, be applied, or also sprayed, to the keratin fibers by employing a brush or similar applicator. As a result of the precipitation reaction between the polysaccharide or the soluble salt thereof and the gel-forming cat ions from gelling composition (C), a film-like gel, which acts like a separating layer similar to a highlighting foil, forms in-situ n the keratin fibers treated with the coloring or lightening agent.

In a second, particularly preferred embodiment of the method, at least one of the aforementioned polysaccharides and/or at least one of the aforementioned salts of the saccharides is present in the form of a hydrous solution or dispersion and, similarly to the gelling composition (C) explained above), is applied to the keratinous fibers after an adequate application of coloring or lightening agent. This can likewise be achieved by employing a brush or similar applicator, preferably however by being sprayed onto the keratin fibers. The hydrous preparation of the polysaccharide, which can gel with calcium ions, is preferably applied first. The gelling composition (C) is then applied.

In a third specific embodiment of the method, at least one of the aforementioned polysaccharides and/or at least one of the aforementioned salts of the polysaccharides is present in the form of a hydrous solution or dispersion. First, the gelling composition (C) explained above is applied to the keratinous fiber strands after an adequate application of coloring or lighting agent. This can be achieved by employing a brush or similar applicator, preferably however by being sprayed onto the keratin fibers. Then, the hydrous preparation of the polysaccharide, which can gel with calcium ions, is applied.

If the coloring or lightening reaction has finished when the recommended application time has lapsed, all of the hair treatment agent can be washed out with water and optionally a shampoo in one single step. The time-consuming processing, as required with the known highlighting foils, is not needed in this case. Since the polysaccharides used as contemplated herein constitute naturally-occurring biopolymers, they are readily bio-degradable in sewage plants. Therefore, they are easier to dispose of than sheet-like foil materials.

Coloring or Lightening Composition (A)

The coloring or lightening composition (A) can be solid, more particularly powdery, but also liquid (from about 0 to about 500 mPas at about 20° C.), medium-viscosity (>from about 400 to about 4000 mPas at about 20° C.), creamy (>from about 4000 to about 40,000 mPas at about 20° C.) or pasty (>from about 40,000 to about 4,000,000 mPas at about 20° C.). Solid coloring or lightening compositions (A) can also exist in tablet or granulated form.

Lightening Compositions (A-1) and (A-2)

In a first preferred embodiment, composition (A) is an agent which, after being mixed with a hydrogen peroxide-including hydrous composition (B), serves to lighten and/or blond keratin fibers, more particularly human hair.

In a first most preferred embodiment, the lightening composition (A-1) is liquid (from about 0 to about 500 mPas at about 20° C.), medium-viscosity (>from about 400 to about 4000 mPas at about 20° C.) or creamy (>from about 4000 to about 40,000 mPas at about 20° C.) and includes water in a quantity of more than from about 7 wt. % to about 90 wt. %, preferably from about 20 to about 85 wt. %, more preferably from about 40 to about 75 wt. %, in each case relative to the weight of the lightening composition (A-1).

In a second most preferred embodiment, the lightening composition (A-2) is solid, more particularly powdery, but can also exist in tablet or granulated form, and includes from about 0 to less than about 7 wt. % water, relative to the weight of the respective lightening composition (A-2).

Coloring Compositions (A-3) and (A-4)

In another preferred embodiment, composition (A) is an agent which, after being mixed with a hydrogen peroxide-including hydrous composition (B), serves to color keratinous fibers, more particularly human hair.

In a third particularly preferred embodiment, the coloring composition (A-3) is liquid (from about 0 to about 500 mPas at about 20° C.), medium-viscosity (>from about 400 to about 4000 mPas at about 20° C.) or creamy (>from about 4000 to about 40,000 mPas at about 20° C.) and includes water in a quantity of more than from about 7 wt. % to about 90 wt. %, preferably from about 20 to about 85 wt. %, more preferably from about 40 to about 75 wt. %, in each case relative to the weight of the coloring composition (A-3), as well as at least one oxidation dye precursor.

In a fourth particularly preferred embodiment, the coloring composition (A-4) is solid, more particularly powdery, but can also exist in tablet or granulated form, and includes from about 0 to less than about 7 wt. % water, relative to the weight of the respective coloring composition (A-4), as well as at least one oxidation dye precursor.

pH Value of the Coloring or Lightening Compositions (A-1) and (A-3)

The coloring or lightening compositions (A-1) and (A-3) have a pH value in the range from about 6.5 to about 12.0, preferably from about 8 to about 11.5, more preferably from about 8.5 to about 11.0, in each case measured at about 20° C.

The coloring or lightening agents (A-2) and (A-4) are solid, preferably powdery, or pasty and include no or only up to approx. 7 wt. % water. In addition, they include a quantity of alkalizing agent such that their about 30 wt. % dispersion in water has a pH value in the range of from about 6.0 to about 12.0, preferably from about 7.5 to about 11.5, most preferably from about 8 to about 11.0, in each case measured at about 20° C.

Alkalizing Agent

The coloring or lightening agents (A), namely (A-1), (A-2), (A-3) and (A-4), include at least one alkalizing agent, selected from ammonium hydroxide, monoethanolamine and sodium silicates, as well as mixtures thereof.

Preferably, the lightening composition (A-1) and the coloring composition (A-3) include ammonium hydroxide, i.e. ammonia in the form of its hydrous solution. The corresponding hydrous ammonia solutions can be from about 10 to about 35% solutions (calculated in wt. % of about 100 g hydrous ammonia solution correspondingly including from about 10 to about 35 g of ammonia). Ammonia in the form of an about 20 to about 30 wt. % solution is preferably used, most preferably in the form of an about 25 wt. % solution.

In a most preferred embodiment, the compositions (A-1) and (A-3) used as contemplated herein are exemplified in that they include ammonium hydroxide in a quantity from about 0.20 to about 18.0 wt. %, preferably from about 1.0 to about 15 wt. %, more preferably from about 2.0 to about 12.0 wt. % and most preferably from about 3.0 to about 9 wt. %—relative to the weight of the composition (A) used as contemplated herein.

In addition to and/or instead of ammonium hydroxide, compositions (A) preferably used as contemplated herein, more particularly the compositions (A-1) and (A-3) used as contemplated herein, include monoethanolamine.

In order to achieve maximum odor minimization and optimize the authenticity properties, monoethanolamine in a total quantity of from about 0.2 to about 9.0 wt. %, preferably from about 1.0 to about 7 wt. %, more preferably from about 2.0 to about 6.0 wt. % and most preferably from about 3.0 to about 5.5 wt. %, relative to the weight of the composition (A) as contemplated herein.

In order to achieve maximum odor minimization and optimize the authenticity properties, the compositions (A-1) and (A-3) as contemplated herein include monoethanolamine in a total quantity of from about 0.2 to about 9.0 wt. %, preferably from about 1.0 to about 7 wt. %, more preferably from about 2.0 to about 6.0 wt. % and most preferably from about 3.0 to about 5.5 wt. %, relative to the weight of the compositions (A-1) or (A-3) as contemplated herein.

Sodium silicates according to the present disclosure are chemical compounds, which are composed of sodium oxide and silicon dioxide, and which can occur in various molar ratios (monosilicate, metasilicate and polysilicate). One example of a sodium silicate, is the sodium salt of ortho silica having the molecular formula $Na_4SiO_4$, which is also referred to as sodium ortho silicate.

Other examples of suitable sodium silicates are di-sodium silicate and/or sodium meta silicate having the molecular formula $Na_2SiO_3$, di-sodium silicate having the molecular formula $Na_2Si_2O_5$ or the di-sodium silicate having the molecular formula $Na_2Si_3O_7$.

Silicates in amorphic form can be produced by melting together silicon dioxide and alkali dioxide in molar ratios of from about 1:1 and about 4:1. The solids thus obtained are dissolved at around 150° C. and 5 bar vapor pressure, in order to obtain a solution of the sodium silicates in water; these corresponding solutions are alkali soluble glasses Solidified, glass-like (amorphous) sodium silicates or the hydrous solutions thereof are referred to as alkali silicates. These are also referred to as sodium silicates. Within this disclosure, sodium soluble glasses are covered by the definition of sodium silicates. The molar composition with soluble glasses is usually from about 2 to about 4 mol $SiO_2$ on 1 mol alkali oxide ($Na_2O$).

One example of a preferred sodium silicate is sodium soluble glass, which exists in the form of its hydrous solution, has a $Na_2O$ content of from about 7.5 to about 8.8 wt. % and at least a $SiO_2$ content of from about 25.0 to about 28.5 wt. % and the CAS No. 1344-09-5 (Chemical Abstracts Number). Other compositions (A) preferred as contemplated herein include, as the alkalizing agent, at least one sodium silicate, preferably sodium meta silicate or sodium soluble glass, in a total quantity of from about 0.1 to about 25 wt. %, preferably from about 0.5 to about 20 wt. %, more preferably from about 1 to about 17 wt. %, most preferably from about 2 to about 9 wt. %, in each case relative to the weight of the composition (A) used as contemplated herein.

The use of sodium silicate as the alkalizing agent is most preferred for the compositions (A-2) and (A-4) used as contemplated herein.

Other preferred compositions (A-2) and (A-4) used as contemplated herein include, as the alkalizing agent, at least one sodium silicate, preferably sodium meta silicate or sodium soluble glass, in a total quantity of from about 0.1 to about 25 wt. %, preferably from about 0.5 to about 20 wt. %, more preferably from about 1 to about 17 wt. %, most preferably from about 2 to about 9 wt. %, in each case relative to the weight of the composition (A-2) or (A-4) used as contemplated herein.

Other preferred compositions (A) used as contemplated herein, more particularly the compositions (A-2) and (A-4, include as the alkalizing agent at least one alkali metal or earth alkali metal carbonate, preferably selected from sodium carbonate, potassium carbonate and magnesium carbonate, as well as mixtures of said carbonates. The at least one alkali metal or earth alkali metal carbonate is preferably included in a total quantity of from about 0.1 to about 25 wt. %, preferably from about 0.5 to about 20 wt. %, more preferably from about 1 to about 10 wt. %, in each case relative to the weight of the composition (A) used as contemplated herein. The at least one alkali metal or earth alkali metal carbonate is preferably included in a total quantity of from about 0.1 to about 25 wt. %, preferably from about 0.5 to about 20 wt. %, more preferably from about 1 to about 10 wt. %, in each case relative to the weight of the composition (A-2) or (A-4) used as contemplated herein.

Other alkalizing agents, such as potassium hydroxide (KOH) and sodium hydroxide (NaOH) can also be included, typically in a total quantity of from about 0.05 to about 1.5 Wt.%, preferably from about 0.1 to about 0.6 wt. %, relative to the weight of the composition (A) used as contemplated herein.

Basic amino acids, more particularly Arginine, Lysine or Histidine, as well as the mixtures of said amino acids, more particularly mixtures of Arginine and Lysine can also be included in preferred compositions (A) as alkalizing agents, preferably in a total quantity of from about 0.01 to about 10 wt. %, more preferably from about 0.1 to about 5 wt. %, most preferably from about 0.5 to about 3 wt. %, in each case relative to the weight of the composition as contemplated herein (A). Compositions (A) most preferred as contemplated herein include mixtures of the aforementioned alkalizing agents, more particularly ammonium hydroxide/ sodium silicate/potassium hydroxide mixtures, ammonium hydroxide/monoethanolamine/sodium silicate/potassium hydroxide mixtures, monoethanolamine/sodium silicate/potassium hydroxide mixtures, ammonium hydroxide/sodium silicate/potassium hydroxide/arginine mixtures, ammonium hydroxide/monoethanolamine/sodium silicate/potassium hydroxide/arginine mixtures, monoethanolamine/sodium silicate/potassium hydroxide/arginine mixtures, sodium silicate/magnesium carbonate mixtures and sodium meta silicate/magnesium carbonate mixtures.

Consistency Enhancers

Compositions (A) used as contemplated herein, more particularly the compositions (A-1) and (A-3), include at least one consistency enhancer. Suitable consistency enhancers are particularly fat substances having a melting point of about 25° C. or over at about 1013 mbar ambient pressure, as well as polymer thickeners, which are different to the polysaccharides, which form a gel with calcium ions in hydrous medium, used as contemplated herein. Such consistency enhancers are preferably selected from linear saturated 1-alkanols having 12 to 30 hydrogen atoms and glyceryl fatty acid esters of general Formula (I),

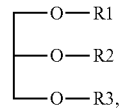

(I)

wherein
R1, R2 and R3 denote, independently of one another, a hydrogen atom or a grouping independent of each other or a grouping of Formula (II),

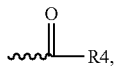
(II)

wherein
R4 denotes an unbranched or branched, saturated or unsaturated C11-C27-alkyl group, on condition that at least one and a maximum of two of the radicals are selected from R1, R3R2 and R3 denotes a grouping of Formula (II). The radical R4 in Formula (II) denotes an unbranched or branched, saturated or unsaturated $C_{11}$-$C_{27}$-alkyl group. R4 preferably denotes an unbranched, saturated $C_{11}$-$C_{27}$-alkyl group. R4 also preferably denotes an unbranched, saturated $C_{13}$-$C_{23}$-alkyl group. R4 most preferably denotes an unbranched, saturated $C_{15}$-$C_{17}$-alkyl group.

Glyceryl fatty acid esters of general Formula (I) most preferred as contemplated herein are selected from at least one compound from the group of Formulas (Ia) to (Id):

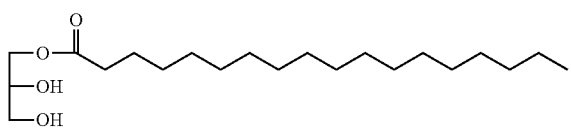
(Ia)

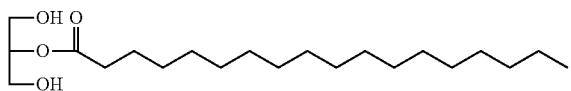
(Ib)

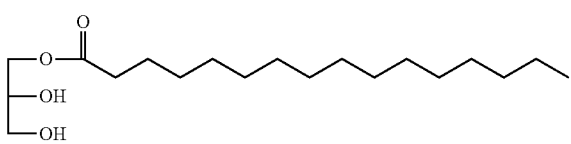
(Ic)

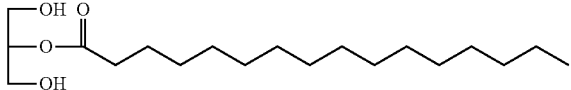
(Id)

The compounds of Formulas (Ia) to (Id) are also known as glyceryl monostearate and glyceryl monopalmitate.

Other coloring or lightening compositions (A) used as contemplated herein are exemplified in that at least one compound from the group of Formulas (Ie) to (Ih) is included as glyceryl fatty acids:

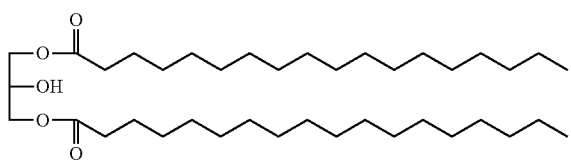
(Ie)

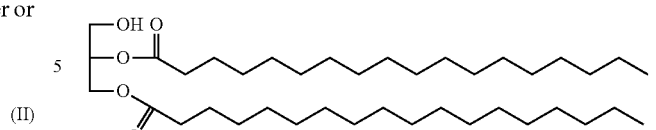
(If)

(Ig)

(Ih)

The compounds of Formulas (Ie) to (Ih) are also known as glyceryl distearate and glyceryl dipalmitate.

Linear saturated 1-alkanols having 12 to 30 carbon atoms are selected from lauryl alcohol, myristyl alcohol, cetyl alcohol, stearyl alcohol, arachidyl alcohol and behenyl alcohol, as well as from mixtures of said alcohols, most preferably from cetyl alcohol, stearyl alcohol, arachidyl alcohol, behenyl alcohol and cetyl alcohol/stearyl alcohol mixtures.

Other consistency enhancers preferred as contemplated herein are ethylene glycolmonosterate, ethylene glycoldistearate, waxes, glycerin triester, which have a boiling point of about 25° C. or over, more particularly hydrated castor oil (castor wax) and ethoxylated, hydrated castor oils, and fatty acid-fatty alcohol esters having a boiling point of about 25° C. or over, as well as mixtures of said substances.

Compositions (A), more particularly compositions (A-1) and (A-3), preferred as contemplated herein include at least one fatty substance consistency enhancer in a total quantity of from about 0.1 to about 30 wt. %, preferably from about 0.5 to about 20 wt. %, more preferably from about 2 to about 15 wt. %, most preferably from about 3 to about 10 wt. %, in each case relative to the weight of the composition (A). Other compositions (A), more particularly compositions (A-1) and (A-3), preferred as contemplated herein include at least one linear saturated 1-alkanol having 12 to 30 hydrogen atoms in a total quantity of from about 0.1 to about 30 wt. %, preferably from about 0.5 to about 20 wt. %, more preferably from about 2 to about 15 wt. %, most preferably from about 3 to about 10 wt. %, in each case relative to the weight of the composition (A).

In a more preferred embodiment of the invention, the compositions (A), (B), (C) as contemplated herein are free of anionic or cationic associative polymers, which are substituted with possibly ethoxylated, $C_6$-$C_{24}$-alkyl- or $C_6$-$C_{24}$-alkenyl groups. In a most preferred embodiment of the invention, the compositions (A), (B) (C) and (D) used as contemplated herein are free of anionic or cationic associative polymers, which are substituted with possibly ethoxylated $C_6$-$C_{24}$-Alkyl- or $C_6$-$C_{24}$-alkenyl groups and selected from acrylates/Ceteth-20 Itaconate copolymers, Polyurethane-39-polymers, acrylates/Beheneth-25 methacrylate copolymers and acrylates/C10-30 alkyl acrylate cross polymers.

Polysaccharide in Composition (A)

Insofar as the at least one polysaccharide, which can gel with calcium ions in a hydrous medium and which is preferably selected from alginic acid, kappa carragheenan, iota carragheenan and pectin, and/or at least one salt of the aforementioned polysaccharides, selected from the alkali metal-, ammonium-, mono-, di- and trialkyl ammonium-, mono-, di- and trialkanolammonium- and magnesium salts, wherein, in the case of salts of the kappa carragheenan its alkali metal salt is only selected from lithium and sodium salts, is included in the coloring or lightening composition (A), it is present in a total amount of from about 0.1 to about 5 wt. %, preferably from about 0.2 to about 3 wt. %, more preferably from about 0.5 to about 2.5 wt. %, in each case relative to the weight of the composition (A). Most preferably, the coloring or lightening composition (A) includes a mixture of alginic acid and sodium alginate in a total quantity of from about 0.1 to about 5 wt. %, more preferably from about 0.2 to about 3 wt. %, most preferably from about 0.5 to about 2.5 wt. %, in each case relative to the weight of the composition (A), wherein the a weight ratio of alginic acid to sodium alginate is preferably in the range of from about 1:2 to about 2:1, more preferably in the range from about 0.8 to about 1.25, most preferably in the weight ratio of about 1:1.

Oxidation Dye Precursor and/or Partially-Oxidizing Hair Dye

When the mixture of the composition (A) and composition (B) used as contemplated herein is intended for oxidative coloring of keratinous fibers, particularly human hair, the composition (A) includes at least one oxidation dye precursor for the formation of the dyes.

The oxidation dye precursors include oxidation dye precursors of the developer type and of the coupler type. Particularly suitable oxidation dye precursors of the developer type are selected from at least one compound from the group of p-phenylenediamine, p-toluylenediamine, 2-(2-hydroxyethyl)-p-phenylenediamine, 2-(1,2-dihydroxyethyl)-p-phenylenediamine, N, N-bis (2-hydroxyethyl)-p-phenylenediamine, 2-methoxymethyl-p-phenylenediamine, N-(4-amino-3-methylphenyl)-N-[3-(1H-imidazol-1-yl) propyl] amine, N, N'-bis (2-hydroxyethyl)-N, N'-bis-(4-aminophenyl)-1,3-diamino-propane-2-ol, bis-(2-hydroxy-5-aminophenyl) methane, 1,3-bis (2,5-diaminophenoxy) propan-2-ol, N, N'-bis (4-aminophenyl)-1,4-diazacycloheptane, 1,10-bis (2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl) phenol, 4-amino-2-(diethylaminomethyl) phenol, 4,5-diamino-1-(2-hydroxyethyl) pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H, 5H-pyrazolo[1,2-a]pyrazol-1-one and the physiologically tolerated salts thereof.

Particularly suitable oxidation dye precursors of the coupler type are selected from the group of 3-aminophenol, 5-amino-2-methylphenol, 3-amino-2-chlor-6-methylphenol, 2-hydroxy-4-aminophenoxy ethanol, 5-amino-4-chlor-2-methylphenol, 5-(2-hydroxyethyl)-amino-2-methylphenol, 2,4-dichlor-3-aminophenol, 2-aminophenol, 3-phenylendiamine, 2-(2,4-diaminophenoxy)ethanol, 1,3-bis(2,4-diaminophenoxy)propane, 1-methoxy-2-amino-4-(2-hydroxyethylamino)benzol, 1,3-bis(2,4-diaminophenyl)propane, 2,6-bis(2'-hydroxyethylamino)-1-methylbenzol, 2-({3-[(2-hydroxyethyl)amino]-4-methoxy-5-methylphenyl}amino) ethanol, 2-({3-[(2-hydroxyethyl)amino]-2-methoxy-5-methylphenyl}amino)ethanol, 2-({3-[(2-hydroxyethyl) amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzol, resorcin, 2-methylresorcin, 4-chlorresorcin, 1,2,4-trihydroxybenzol, 2-amino-3-hydroxypyridin, 3-amino-2-methylamino-6-methoxypyridin, 2,6-dihydroxy-3,4-dimethylpyridin, 3,5-diamino-2,6-dimethoxypyridin, 1-phenyl-3-methylpyrazol-5-on, 1-naphthol, 1,5-dihydroxynaphthalin, 2,7-dihydroxynaphthalin, 1,7-dihydroxynaphthalin, 1,8-dihydroxynaphthalin, 4-hydroxyindol, 6-hydroxyindol, 7-hydroxyindol, 4-hydroxyindolin, 6-hydroxyindolin, 7-hydroxyindolin or mixtures of said compounds or the physiologically compatible salts thereof, particularly the sulfates, hydrogen sulfates, chlorides and hydrochlorides.

Particular preference is given to 4,5-diamino-1-(2-hydroxyethyl)pyrazol, 4-amino-3-methylphenol, 4-amino-2-hydroxytoluene and m-aminophenol, as well as mixtures of these dye precursors.

In a most preferred embodiment, the compositions (A) used as contemplated herein include one or multiple oxidation dye precursors in a total amount of from about 0.01 to about 30.0 wt. %, preferably from about 0.1 to about 15 wt. %, more preferably from about 0.6 to about 3.1 wt. % and particularly from about 1.2 to about 2.2 wt. %, relative to the weight of the composition (A) used as contemplated herein.

In a further preferred embodiment, the compositions (A) as contemplated herein include at least one partially-oxidizing dye. Partially-oxidizing dyes can be sub-divided into anionic, cationic and non-ionic partially-oxidizing dyes. The partially-oxidizing dyes are preferably selected from the nitrophenylenediamines, the nitroaminophenols, the azo dyes, the anthraquinones, the triarylmethane dyes or the indophenols and the physiologically acceptable salts thereof. Preferably, at least one partially-oxidizing dye is included in a total quantity of from about 0.001 to about 3 wt. %, relative to the weight of the composition (A) as contemplated herein. Partially-oxidizing dyes are used in oxidative coloring agents (A-3) and (A-4) for a nuancing of the achieved color tone and in oxidative bleaching agents (A-1) and (A-2) to compensate for undesired red and orange tones which can develop during the decomposition of the hair's melanin.

Preferred anionic partially-oxidizing dyes are the compounds known under the international designations and/or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue and tetrabromophenol blue. Tetrabromophenol blue, Acid Red 33 and Acid Red 52, as well as the mixtures thereof are most preferred for bleaching agents (A-1) and (A-2) as contemplated herein.

Preferred partially-oxidizing dyes are cationic triphenylmethane dyes, such as Basic Blue 7, Basic Blue 26, Basic Violet 2 and Basic Violet 14, aromatic systems, which are substituted with a quaternary nitrogen group, such as Basic Yellow 57, Basic Red 76, Basic Blue 99, Basic Brown 16 and Basic Brown 17, cationic anthraquinone dyes, such as HC Blue 16 (Bluequat B), as well as partially-oxidizing dyes including a heterocycle, which has at least one quaternary nitrogen atom, more particularly Basic Yellow 87, Basic Orange 31 and Basic Red 51. The cationic partially-oxidizing dyes, which are sold under the trade name of Arianor, are also preferred cationic partially-oxidizing dyes as contemplated herein.

Suitable non-ionic substantive dyes are, in particular, non-ionic nitro and quinone dyes and neutral azo dyes.

Preferred nonionic partially-oxidizing coloring agents are the compounds known under the international designations and/or trade name HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzol, 2-amino-4-nitrophenol, 1,4-bis-(2-hydroxyethyl)-amino-2-nitrobenzol, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzol, 1-amino-4-(2-hydroxyethyl)amino-5-chlor-2-nitrobenzol, 4-amino-3-nitrophenol, 1-(2'-Ureidoethyl) amino-4-nitrobenzol, 2-[(4-amino-2-nitrophenyl)amino] benzoic acid, 4-[(3-hydroxypropyl)amino]-3-nitrophenol, 4-nitro-o-phenylendiamine, 6-nitro-1,2,3,4-tetrahydrochinoxaline, 2-hydroxy-1,4-naphthoquinone, picramic acid and the salts thereof, 2-amino-6-chloro-4-nitrophenol, 4-ethylamino-3-nitrobenzoic acid and 2-chlor-6-ethylamino-4-nitrophenol are particularly preferred.

Oxidation Composition (B)
Hydrogen Peroxide

The formation of the dye in oxidative coloring agents and/or the decomposition hair's own dye melanin for bleaching takes place due to the influence of a peroxide compound as the oxidant. Hydrogen peroxide is typically used for this purpose. Hydrogen peroxide can be used only in the form of a hydrous solution.

Oxidant compositions (B) preferred as contemplated herein are exemplified in that they include from about 0.5 to about 13 wt. %, preferably from about 1 to about 9 wt. %, more preferably from about 2 to about 7 wt. % and most preferably from about 3 to about 4.5 wt. % hydrogen peroxide (calculated as 100% $H_2O_2$), in each case relative to the total weight of the oxidation composition (B).

Bleaching agents (A-2) or coloring agents (A-4), which are able to achieve a dramatic lightening effect, for example for the coloring of very dark, melanin-rich keratinous fibers, can also include strongly oxidizing peroxide compounds such as potassium, sodium and/or ammonium persulfate and/or sodium percarbonate.

Water

The oxidation compositions (B) used as contemplated herein include water, specifically in a quantity of from about 20 to about 95 wt. %, preferably from about 30 to about 90 wt. %, more preferably from about 40 to about 85 wt. %, most preferably from about 50 to about 80 wt. %, in each case relative to the total weight of the oxidation composition (B).

pH Value

Oxidant compositions (B) used as contemplated herein have a pH value in the range from about 2.5 to about 6.5, preferably in the range from about 3 to about 5.5, more particularly in the range from about 3.5 to about 5.0, in each case measured at about 20° C.

Polysaccharide in the Oxidation Composition (B)

Insofar as the at least one polysaccharide, which can gel with calcium ions in a hydrous medium and which is preferably selected from alginic acid, kappa carragheenan, iota carragheenan and pectin, and/or at least one salt of the aforementioned polysaccharides, selected from the alkali metal-, ammonium-, mono-, di- and trialkyl ammonium-, mono-, di- and trialkanolammonium- and magnesium salts, wherein, in the case of salts of the kappa carragheenan its alkali metal salt is only selected from lithium and sodium salts, is included in the oxidation composition (B), it is present in a total amount of from about 0.1 to about 5 wt. %, preferably from about 0.2 to about 3 wt. %, more preferably from about 0.5 to about 2.5 wt. %, in each case relative to the weight of the composition (B). Most preferably, the oxidation composition (B) includes a mixture of alginic acid and sodium alginate in a total quantity of from about 0.1 to about 5 wt. %, more preferably from about 0.2 to about 3 wt. %, most preferably from about 0.5 to about 2.5 wt. %, in each case relative to the weight of the composition (B), wherein the a weight ratio of alginic acid to sodium alginate is preferably in the range of from about 1:2 to about 2:1, more preferably in the range from about 0.8 to about 1.25, most preferably in the weight ratio of about 1:1.

Organic Solvents

Moreover, all compositions used as contemplated herein, more particularly the oxidation compositions (B) and the coloring or lightening compositions (A-1) and (A-3), less preferably also (A-2) and (A-4), may include at least one organic solvent, which is preferably selected from one or more mono- or polyvalent alcohols having from about 2 to about 9 carbon atoms, polyethylene glycols having from about 2 to about 20 ethylene glycol units, as well as mixtures of said solvents, preferably in a total quantity from about 0.001 to about 80 wt. %, more preferably from about 0.01 to about 50 wt. %, even more preferably from about 0.5 to about 20 wt. %, most preferably from about 1.5 to about 10 wt. %, in each case relative to the weight of the composition used as contemplated herein. Preferred organic solvents are selected from C1-C4-alcohols, more particularly ethanol and isopropanol, also selected from polyvalent alcohols having from about 2 to about 9, preferably selected from 1,2propylene glycol, 2-methyl-1,3-propanediol, glycerine, butylene glycols such as 1,2-butylene glycol, 1,3-butylene glycol and 1,4-butylene glycol, pentylene glycols such as 1,2-pentanediol and 1,5-pentanediol, hexanediols such as 1,2-hexanediol and 1,6-hexanediol, hexanetriols such as 1,2,6-hexanetriol, 2-ethyl-2-hydroxymethyl-1,3-propanediol, dipropylene glycol, tripropylene glycol, diglycerin and triglycerine, and also selected from polyethylene glycols having from about 2 to about 20 ethylene glycol units, more particularly PEG-3, PEG-4, PEG-6, PEG-7, PEG-8, PEG-9, PEG-10, PEG-12, PEG-14, PEG-16, PEG-18 and PEG-20, as well as the mixtures thereof, PEG-3 to PEG-8 being preferred. The use of mixtures of the aforementioned substances is preferred as contemplated herein.

Mixture Ratios (A) (B)

Moreover, for the coloring or lightening result, it is important for the ready-to-use coloring or lightening agent, which is obtained by mixing coloring or lightening composition (A) with an oxidation composition (B) used as contemplated herein, to have a pH value in the range of from about 6.5 to about 11.0, preferably from about 8 to about 10.5, more preferably from about 8.5 to about 9.5, in each case measured at about 20° C. At such pH values, the outer keratin fiber layer opens to the optimal extent to absorb the oxidation dye precursor, and the oxidative effect of the hydrogen peroxide and possibly other peroxide compounds develops to the optimal extent.

It can also be preferred as contemplated herein for the ready-to-use coloring or lightening agent to be produced by mixing a lightening composition (A-1) as contemplated herein with a lightening composition (A-2) used as contemplated herein and an oxidation composition (B) used as contemplated herein.

It can also be preferred as contemplated herein for the ready-to-use coloring or lightening agent to be produced by mixing a lightening composition (A-3) as contemplated herein with a lightening composition (A-2) used as contemplated herein and an oxidation composition (B) used as contemplated herein.

Methods, preferably multi-tone color changing of keratinous fibers, preferred as contemplated herein, are therefore exemplified in that the weight ratio of coloring or lightening agent (A) or oxidation composition (B) is in the range of from about 1:10 to about 4:1, preferably in the range of from about 1:5 to about 3:1, more preferably in the range of from about 1:4 to about 2:1 and most preferably in the range of from about 1:2 to about 1:1.

In order to promote the miscibility of (A) and (B) and the ability of the coloring agent to be washed out of the keratinous fibers at the end of the method as contemplated herein, it is preferred as contemplated herein for at least the coloring or lightening composition (A) to include at least one surfactant, preferably in a total quantity of from about 0.1 to about 15 wt. %, preferably from about 1 to about 8 wt. %, relative to the weight of the composition (A).

The composition (B) also preferably includes at least one surfactant, preferably in a total quantity of from about 0.1 to about 10 wt. %, preferably from about 1 to about 5 wt.-%, relative to the weight of the composition (B).

Suitable surfactants, more particularly for (A) and (B), are non-ionic, anionic, cationic and amphoteric surfactants. Non-ionic and anionic surfactants, as well as mixtures thereof, are preferred. Preferred anionic surfactants are alkyl sulfates, alkyl ether sulfates and ether carboxylic acids having from about 10 to about 18 C-atoms per alkyl group and up to about 12 glycol ether groups per molecule. Particularly preferred amphoteric surfactants are N-cocoalkylaminopropionate, cocoacylaminoethylaminopropionate and $C_{12}$-$C_{18}$ acylsarcosin.

Preferred non-ionic surfactants are selected from ethoxylated $C_{10}$-$C_{24}$ fatty alcohols having an ethoxylation degree of from about 4 to about 120, preferably from about 10 to about 50, more preferably from about 12 to about 20, wherein mixtures of said ethoxylated $C_{10}$-$C_{24}$ fatty alcohols with various degrees of ethoxylation are preferred. Other preferred non-ionic surfactants are selected from ethoxylated glycerinmono-, -di- and -triesters of C10-C24 fatty acids, for example PEG-40 Castor Oil, PEG-40 Hydrogenated Castor Oil, PEG-60 Castor Oil or PEG-60 Hydrogenated Castor Oil. Other preferred non-ionic surfactants are selected from $C_8$-$C_{22}$-alkylmono- and -oligoglycosides. $C_8$-$C_{22}$-alkylmono- and -oligoglycosides are known, commercially available surfactants and emulsifiers. They are produced in particular by converting glucose or oligosaccharides with primary alcohols having 8 to 22 carbon atoms. With respect to the glycoside radical, both monoglycoside, wherein a cyclic sugar radical is glycosidically bound to the fatty alcohol, and also oligomer glycosides having an oligomerization degree to approx. 8, preferably from about 1 to about 2 are suitable. The degree of oligomerization is a statistical mean value, which is used as the basis of a homologous distribution typical for such technical products. Commercially-available products, which can be obtained for example under the trade name of Plantacare®, include a $C_8$-$C_{16}$-alkyl group glucosidically bound to an oligoglucoside radical, the mean oligomerization degree of which is from about 1 to about 2, more particularly from about 1,2 to about 1,4. Most preferred from about $C_8$ to about $C_{22}$-alkylmono- and -oligoglycosides are selected from octylglucoside, decylglucoside, lauryl glucoside, palmityl glucoside, isostearyl glucoside, stearyl glucoside, arachidyl glucoside and behenyl glucoside, as well as the mixtures thereof.

Preferred cationic surfactants include ammonium halogenides, more particularly chlorides and bromides, such as alkyltrimethyl ammonium chlorides, dialkyldimethyl ammonium chlorides and trialkylmethyl ammonium chlorides, e.g. cetyltrimethyl ammonium chloride, stearyltrimethyl ammonium chloride, distearyldimethyl ammonium chloride, lauryldimethyl ammonium chlorides, lauryldimethylbenzyl ammonium chloride and tricetylmethyl ammonium chloride, as well as the imidazolium compounds known under the INCI trade names of Quaternium-27 and Quaternium-83.

Gelling Composition (C)

In order to produce the separating layer an effect similar to that of the barrier layer from polysaccharide gel in-situ on the keratin fibers, a gelling composition (C) is applied to the keratinous fibers after application of the mixture (M) of coloring or lightening composition (A) and oxidant composition (B), for example by employing a brush or similar applicator or—most preferably—by spraying, wherein the gel composition (C) includes:

c)i. from about 0.1 to about 3 wt. %, preferably from about 0.2 to about 2 wt. %, more preferably from about 0.4 to about 1 wt. %, relative to the weight of the composition (C), at least one salt of a multivalent metal ion, selected from calcium-, strontium-, barium- and aluminum salts having a water solubility at about 20° C. of at least about 500 mg/l, and also if the polysaccharide, which forms a gel with calcium ions, comprises kappa carragheenan or a salt thereof, the gelling composition (C) including from about 0.1 to about 3 wt. %, preferably from about 0.2 to about 2 wt. %, more preferably from about 0.4 to about 1 wt. %, relative to the weight of the composition (C), at least one salt, selected from potassium, calcium-, strontium-, barium- and aluminums salts having a water solubility at about 20° C. of at least about 500 mg/l, c)ii. from about 50 to about 99 wt. %, relative to the weight of the composition (C), water, c)iii. optionally at least one cation polymer, which is preferably selected from cationized guar ethers.

c)iv. wherein the gelling composition (C) has a pH value in the range from about 4 to about 12, preferably in the range of from about 4 to about 9, most preferably from about 6.5 to about 8, measured at about 20° C.;

In preliminary testing which led to the present disclosure, it was found that incorporation of a calcium salt having a water solubility of at least about 500 mg/l at about 20° C. into a coloring composition (A-3) as contemplated herein significantly impaired the development of the dye and the coloring of the keratinous fibers under the influence of hydrogen peroxide. No detrimental effects on this embodiment were observed for lightening and bleaching methods.

Gel-Forming Salt/Water Solubility

At about 20° C., the at least one salt c)i has a water solubility of at least about 500 mg/l, preferably of at least about 40 g/l, more preferably of at least about 200 g/l, and most preferably of at least about 350 g/l. The preferred calcium chloride as contemplated herein has a water solubility of about 740 g/l at about 20° C. Other most preferred salts c)i as contemplated herein are selected from calcium acetate (water solubility 374 g/l), calcium lactate, calcium gluconate and calcium gluconate lactate. Aluminum chloride, aluminum hydroxychloride, aluminum sulfate, aluminum lactate, aluminum acetate and aluminum gluconate are likewise preferred. Potassium chloride, potassium acetate, potassium lactate, potassium gluconate and potassium sulfate are preferred for the gelling of kappa carragheenan, potassium, chloride, potassium lactate, and potassium gluconate being most preferred. Strontium chloride and barium chloride are also suitable. Preferably, mixtures of the aforementioned salts can also be included.

More preferably, the gelling composition (C) includes at least one salt, selected from calcium chloride, calcium lactate, calcium gluconate and calcium gluconolactate, as well as mixtures thereof in a total quantity of from about 0.1 to about 5 wt. %, more preferably from about 0.2 to about 3 wt.-%, most preferably from about 0.5 to about 2.5 wt. %, in each case relative to the weight of the composition (C). Most preferably, the gelling composition (C) includes from about 0.1 to about 5 wt. %, more preferably from about 0.2 to about 3 wt. %, most preferably from about 0.5 to about 2.5 wt. %, calcium chloride, in each case relative to the weight of the composition (C).

The gelling composition (C) includes, in each case relative to its weight, from about 50 to about 99 wt. %, preferably from about 70 to about 95 wt. %, more preferably from about 75 to about 92 wt. % water.

The gelling composition (C) has a pH value in the range from about 4 to about 12, preferably in the range of from about 4 to about 9, more preferably from about 6.5 to about 8, measured at about 20° C. The setting of an acid or an alkali pH depends in part whether the viscosity of the composition (C) for improving the application characteristics thereof, more particularly the spray pattern, is to be increased by employing a thickening agent. Cationic polymers are particularly suitable for promoting moderate thickening of the composition (C). Preferred cationic polymers are selected from cationic guar derivatives, particularly from cationized guar ethers, more particularly from polymers having the INCI designations Hydroxypropyl Guar Hydroxypropyltrimonium Chloride and Guar hydroxypropyltrimonium Chloride. Insofar as the gelling composition (C) includes a cationic polymer, said polymer is included in a total quantity of from about 0.01 to about 1 wt. %, preferably from about 0.1 to about 0.8 wt. %, more preferably from about 0.2 to about 0.5 wt. %, in each case relative to the weight of the composition (C). Insofar as the gelling composition (C) includes a cationic polymer, said polymer preferably has a pH value in the range of from about 4 to about 6.5, measured at about 20° C.

Just like for the other compositions used as contemplated herein, the pH value is set by employing typical pH setting agents, more particularly citric acid, lactic acid, NaOH, KOH and similar cosmetically-tolerable acids and alkalis.

In a preferred embodiment of the color-changing method as contemplated herein, the gelling composition (C) is produced in-situ or only from about 0.01 to about 24 hours before the method as contemplated herein is applied by mixing a solid, preferably powdery gelling composition (C'), including the at least one salt mentioned under c)i in powder form and optionally at least one cation polymer, which is preferably selected from cationized guar ethers, in powder form, with water c) iii, Most preferably, the gelling composition (C') additionally includes a solid, preferably powdery, pH setting agent, e.g. an acid such as citric acid, and/or an alkalizing agent, such as sodium silicate.

Polysaccharide Composition (D)

A particularly preferred embodiment of the color-changing method as contemplated herein the at least one polysaccharide, which can form a gel with calcium ions in an aqueous medium and which is preferably selected from alginic acid, kappa carragheenan, iota carragheenan and pectin, and/or at least one salt of the aforementioned polysaccharides, selected from the alkali metal-, ammonium-, mono-, di- and trialkyl ammonium-, mono-, di- and trialkanolammonium- and magnesium salts, wherein in the case of salts of the kappa carragheenan, the alkali metal salt thereof is selected only from lithium- and sodium salts, is prepared in the form of a polysaccharide composition (D), including d)i. at least one polysaccharide, which can form a gel with calcium ions in hydrous medium and which is selected from alginic acid, kappa carragheenan, iota carragheenan and pectin, and/or at least one salt of the aforementioned polysaccharide, selected from the alkali metal-, ammonium-, mono-, di- and trialkyl ammonium-, mono-, di- and trialkanol ammonium- and magnesium salts, preferably in a total quantity of from about 0.1 to about 5 wt. %, preferably from about 0.5 to about 2 wt. %, more preferably from about 0.5 to about 2.5 wt. %, in each case relative to the weight of the composition (D), wherein in the case of the kappa carragheenan, the alkali metal salt is selected only from lithium- and sodium salts, d)ii. from about 50 to about 99.9, preferably from about 60 to about 95, more preferably from about 80 to about 90 wt. % water, in each case relative to the weight of the composition (D), d)iii. optionally at least one alkalizing agent, which is preferably selected from powdery sodium silicates, more particularly sodium meta silicates, d)iv. optionally at least one polymer, including (meth)acrylic acid-, (meth)acrylic acid-, (meth)acrylamide- and/or 2-acrylamido-2-methylpropane sulfonic acid monomers, preferably in a total quantity of from about 0.05 to about 3 wt. %, preferably from about 0.2 to about 0.5 wt. %, relative to the weight of the composition (D), d)v. optionally at least one oil in a total quantity of from about 0.1 to about 10 wt. %, preferably from about 0.3 to about 5 wt. %, more preferably from about 1 to about 3 wt. %, in each case relative to the weight of the polysaccharide composition (D), wherein optionally the polysaccharide composition (D) is produced by mixing a solid, preferably powdery, polysaccharide composition (D'), including d)i and optionally d)iii and/or optionally d)iv, with the component d)ii and optionally with the component d)v in situ or from about 0.01 to about 24 hours before applying the color-changing method as contemplated herein, In a preferred embodiment of the color-changing method as contemplated herein, the polysaccharide composition (D) is produced in situ or from about 0.01 to about 24 hours before the color-changing method as contemplated herein is applied, by mixing a solid, preferably a powdery, polysaccharide composition (D'), including c)i and optionally d)iii and/or optionally d)iv, with the component d)ii and optionally with the component d)v.

For the in situ production of the polysaccharide composition (D), it has proven useful for at least one polysaccharide, which can form a gel with calcium ions in a hydrous medium, to be dissolved in from about 25° C. to about 40° C. warm water including at least one oil in a total quantity of from about 0.1 to about 10 wt. %, preferably from about 0.3 to about 5 wt. %, most preferably from about 1 to about 3 wt. %, in each case relative to the weight of the polysaccharide composition (D). The oil ought to be included in the water before the polysaccharide is added. This significantly accelerates the dissolution of the polysaccharide. Oils most preferred as contemplated herein are selected from natural and synthetic hydrocarbons, preferably from mineral oils, paraffin oils, $C_{18}$-$C_{30}$-isoparaffins, more particularly isoeicosan, polyisobutenes and polydecenes, also selected from $C_8$-$C_{16}$-isoparaffins, more particularly from isodecane, isododecane, isotetradecane and isohexadecane, as well as mixtures thereof, as well as 1,3-di-(2-ethylhexyl)-cyclohexane.

Other oils preferred as contemplated herein are selected from the esters of linear or branched saturated or unsaturated fatty alcohols with 2 to 30 carbon atoms having linear or branched saturated or unsaturated fatty alcohols having 2 to 30 carbon atoms which can be hydroxylated. This includes cetyl-2-ethylhexanoate, 2-hexyldecylstearate (e.g. Eutanol® G S), 2-hexyldecyllaurate, isodecylneopentanoate, isononylisononanoate, 2-ethylhexylpalmitate (e.g. Cegesoft® C 24) and 2-ethylhexylstearate (e.g. Cetiol® 868). Preference is also given to isopropylmyristate, isopropylpalmitate, isopropylstearate, isopropylisostearate, isopropyloleate, isooctylstearate, isononylstearate, isocetylstearate, isononylisononanoate, isotridecylisononanoate, cetearylisononanoate, 2-ethylhexyllaurate, 2-ethylhexylisostearate, 2-ethylhexylcocoate, 2-octyldodecylpalmitate, butyloctanoic acid-2-butyloctanoate, diisotridecylacetate, n-butylstearate, n-hexyllaurate, n-decyloleate, oleyloleate, oleylerucate, erucyloleate, erucylerucate, ethylene glycoldioleate and ethylene glycoldipalmitate.

Additional oils preferred as contemplated herein are selected from the benzoic acid esters of linear or branched C8-22-alkanols. Particular preference is given to benzoic acid-C12-C15-alkyl esters, e.g. available as the commercial product Finsolv® TN, benzoic acid isostearyl esters, e.g. available as the commercial product Finsolv® SB, ethylhexylbenzoate, e.g. available as the commercial product Finsolv® EB, and benzoic acid octyldocecyl esters, e.g. available as the commercial product Finsolv® BOD.

Further oils as contemplated herein are selected from fatty alcohols having 6 to 30 carbon atoms, which are unsaturated or branched and saturated or branched and unsaturated. The branched alcohols are often also referred to as Guerbet alcohols, as they are obtained by the Guerbet reaction. Preferred alcohols are 2-hexyldecanole (Eutanol® G 16), 2-octyldodecanole (Eutanol® G), 2-ethylhexyl alcohol and isostearylalcohol.

Further preferred oils are selected from Guerbet alcohols and Guerbet alcohol esters, e.g. from the commercial product Cetiol® PGL (2-Hexyldecanol and 2-Hexyldecyllaurate).

Additional cosmetic oils preferred as contemplated herein are selected from the triglycerides (=triple esters of glycerin) of linear or branched, saturated or unsaturated, if applicable hydroxylated C8-30 fatty acids. Particular preference is given to the use of natural oils, such as amaranthus seed oil, apricot kernel oil, arganil, avocado oil, babassu oil, cotton seed oil, borage oil, camel oil, safflower oil, peanut oil, grenadine core oil, grapefruit seed oil, hemp oil, hazelnut oil, hollowseed oil, currant seed oil, jojoba oil, linseed oil, macadamia nut oil, corn oil, almond oil, marula oil, evening primrose oil, olive oil, palm oil, palm kernel oil, parannut oil, pectic oil, peach kernel oil, rapeseed oil, castor oil, sandalwood oil, sanddornkernel oil, sesame oil, soya oil, sunflower oil, grapeseed oil, walnut oil, wild-type oil, wheat germ oil, and the liquid fractions of coconut oil and the like. However, preference is also given to synthetic triglyceride oils, particularly capric/caprylic triglycerides, i.e. the commercial products Myritol® 318, Myritol® 331 (BASF) or Miglyol® 812 (Hüls) having unbranched fatty acid esters and glyceryl triisostearin with branched fatty acids.

Additional particularly preferred cosmetic oils as contemplated herein are selected from the dicarboxylic acid esters of linear or branched C2-C10 alkanols, particularly diisopropyl adipate, di-n-butyl adipate, di (2-ethylhexyl) adipate, dioctyl adipate, diethyl/di-n-butyl/dioctyl sebacate, diisopropyl sebacate, dioctyl malate, dioctyl maleate, dicaprylyl maleate, diisooctyl succinate, di-2-ethylhexyl succinate and di-(2-hexyldecyl) succinate.

Additional preferred cosmetic oils as contemplated herein are selected from the adducts of 1 to 5 propylene oxide units on mono- or multivalent C8-22 alkanols, such as octanol, decanol, decanediol, lauryl alcohol, myristyl alcohol and stearyl alcohol, e.g. PPG-2 myristyl ether and PPG-3 myristyl ether (e.g. Witconol® APM).

Additional preferred cosmetic oils as contemplated herein are selected from the adducts of at least about 6 ethylene oxide and/or propylene oxide units on mono- or polyvalent C3-22 alkanols, such as glycerin, butanol, butanediol, myristyl alcohol and stearyl alcohol, which can be optionally esterified, such as PPG-14 butyl ether (Ucon Fluid® AP), PPG-9 butyl ether (e.g. Breox® B25), PPG-10 butanediol (Macol® 57), PPG-15 stearyl ether (Arlamol® E) and glycereth-7-diisononanoate.

Additional preferred cosmetic oils as contemplated herein are selected from the C8-C22 fatty alcohol esters of monovalent or multivalent C2-C7 hydroxy carboxylic acids, particularly the esters of glycolic acid, lactic acid, malic acid, tartaric acid, citric acid and salicylic acid. Such esters based on linear C14/15 alkanols, such as C12-C15 alkyl lactate, and on C12/13 alkanols branched in 2-position are commercially available under the trade name Cosmacol® from Nordmann Rassmann GmbH & Col, Hamburg, particularly the commercial products Cosmacol® ESI, Cosmacol® EMI and Cosmacol® ETI.

Additional preferred cosmetic oils as contemplated herein are selected from the symmetrical, asymmetrical or cyclical esters of carboxylic acid with $C_{3-22}$ alkanols, $C_{3-22}$ alkanediols or $C_{3-22}$ alkanetriols, e.g. dicaprylylcarbonate (Cetiol® CC) or the esters according to the teaching of DE19756454 A1, particularly glycerin carbonate.

Additional cosmetic oils that can be preferred as contemplated herein are selected from the esters of dimeric unsaturated $C_{12}$-$C_{22}$ fatty acids (dimeric fatty acids) with monovalent linear, branched or cyclical $C_2$-$C_{18}$ alkanols or multivalent linear and branched $C_2$-$C_6$ alkanols.

Additional cosmetic oils that are suitable as contemplated herein are selected from the silicone oils, which include, for example, dialkyl- and alkylaryl siloxanes, such as cyclopentadienyl, cyclohexsiloxane, dimethylpolysiloxane and methylphenylpolysiloxane, but also hexamethyldisiloxane, octamethyltrisiloxane and decamethyltetrasiloxane. Preference can be given to volatile silicone oils which can be cyclic, such as octamethylcyclotetrasiloxane, decamethylcyclopentasiloxane and dodecamethylcyclohexsiloxane, and mixtures thereof, as are included, for example, in the commercial products DC 244, 245, 344 and 345 of Dow Corning. Volatile silicone oils are also suitable, particularly hexamethyldisiloxane ($L_2$), octamethyltrisiloxane ($L_3$), decamethyltetrasiloxane ($L_4$) and any double and trouble mixtures of $L_2$, $L_3$ and/or $L_4$, preferable such mixtures which are commercially available, for example, in the products DC 2-1184, Dow Corning® 200 (0.65 cSt) and Dow Corning® 200 (1.5 cSt) from Dow Corning. Preferred nonvolatile silicone oils are selected from higher molecular linear dimethylpolysiloxanes, commercially available, for example, under the name Dow Corning® 200 Fluid with kinematic viscosities (25° C.) in a range of from about 5 to about 100 cSt, preferably from about 5 to about 50 cSt or also from about 5 to about 10 cSt, and dimethylpolysiloxane with a kinematic viscosity (25° C.) of approximately 350 cSt. As contemplated herein, the use of mixtures of the aforementioned oils is most preferred.

The dissolution of the polysaccharide can also be promoted by adding a surfactant, for example in a total quantity of from about 0.05 to about 3 wt. %, preferably from about 0.1 to about 1 wt. %, more preferably from about 0.3 to about 0.8 wt. %, relative to the weight of the composition (D). However, a surfactant can cause the polysaccharide composition (D), which ought to be shaken to loosen the polysaccharide, to foam too strongly, making it difficult to apply. The polysaccharide composition (D) therefore preferably includes no surfactant.

Most preferably used polysaccharide compositions (D) and (D') are exemplified in that the at least one polysaccharide, which can form a gel with calcium ions in hydrous medium, is selected from alginic acid, sodium alginate, ammonium alginate, magnesium alginate, monoethanolammoniumalginate, kappa carragheenan, the lithium salt of kappa carragheenan, the sodium salt of kappa carragheenan, iota carragheenan, the lithium salt of iota carragheenan, the sodium salt of iota carragheenan, the potassium salt of iota carragheenan, the ammonium salt of iota carragheenan, pectin, sodium pectinate, ammonium pectinate, potassium pectinate and magnesium pectinate, as well as mixtures of said substances. Most preferred mixtures as contemplated herein are those from alginic acid and sodium alginate, more particularly mixtures from alginic acid and sodium alginate in the weight ratio of alginic acid to sodium alginate in the range of from about 1:2 to about 2:1, preferably in the range from about 0.8 to about 1.25, most preferably in the weight ratio of about 1:1.

Most preferably, the polysaccharide composition (D) includes a mixture of alginic acid and sodium alginate in a total quantity of from about 0.1 to about 5 wt. %, more preferably from about 0.2 to about 3 wt. %, most preferably from about 0.5 to about 2.5 wt. %, in each case relative to the weight of the composition (D), wherein the a weight ratio of alginic acid to sodium alginate is preferably in the range of from about 1:2 to about 2:1, more preferably in the range from about 0.8 to about 1.25, most preferably in the weight ratio of about 1:1.

As contemplated herein, the polysaccharide composition (D) has a pH value in the range from about 7 to about 12, preferably in the range from about 8 to about 10, most preferably from about 8.5 to about 9.5, measured at about 20° C. Therefore, the polysaccharide composition (D) preferably includes at least one alkalizing agent, which is preferably selected from powdery sodium silicates, more preferably powdery sodium meta silicates. The other aforementioned alkalizing agents can also be used to set the pH value of the polysaccharide composition (D). For the polysaccharide composition (D'), a content of at least one solid, preferably powdery, alkalizing agent is preferred, which is preferably selected from powdery sodium silicates, more particularly powdery sodium meta silicates.

As contemplated herein, it may be preferable for the polysaccharide composition (D) polysaccharide composition (D') to include at least one polymer, including (meth)acrylic acid, (meth)acrylate-, (meth)acrylamide- and/or 2-acrylamido-2-methylpropansulfonic acid monomers, preferably in a total quantity of from about 0.05 to about 3 wt. %, more preferably from about 0.2 to about 0.5 wt. %, relative to the weight of the composition (D), The addition of said polymers serves primarily to improve the solubility of the polysaccharide during the in situ production of the composition (D). Preferably, the at least one polymer, including (meth)acrylic acid (meth)acrylate-, (meth)acrylamide- and/or 2-acrylamido-2-methylpropansulfonic acid monomers, is selected from cross-linked homopolymers of the acrylic acid, cross-linked homopolymers of 2-acrylamido-2-methylpropansulfonic acid, cross-linked copolymers comprising acrylic acid- and 2-acrylamido-2-methylpropansulfonic acid units, cross-linked copolymers comprising 2-methyl-2[(1-oxo-2-propenyl)amino]-1-propansulfonic acid units and hydroxyethylacrylate units, cross-linked copolymers comprising acrylamide- and 2-acrylamido-2-methylpropansulfonic acid units, cross-linked copolymers comprising methacrylic acid units and C1-C4-alkylacrylate units, cross-linked copolymers comprising acrylic acid units and C1-C4-alkylmethacrylate units, as well as mixtures thereof.

Most preferably, the at least one polymer, including (meth)acrylic acid-, (meth)acrylate-, (meth)acrylamide- and/or 2-acrylamido-2-methylpropansulfonic acid monomers, having no monomers, which are substituted with possibly ethoxylated, $C_6$-$C_{24}$-alkyl- or $C_6$-$C_{24}$-alkenyl groups;

As contemplated herein, there are three embodiments of the color-changing method for use of the polysaccharide composition (D).

A first preferred color-changing method as contemplated herein the polysaccharide composition (D) is applied in a method step after the application step e and before application, preferably spraying, of the gelling composition (C) on the keratinous fibers treated with the mixture (M) of (A) and (B).

This method is most preferred, because the best separating force is produced, i.e. between adjacent keratinous fiber strands with different colors despite coming into contact with each other during the application time. There is no color shift with this method.

A second preferred color-changing method as contemplated herein the polysaccharide composition (D) is added in a method step before the application step e to one of the compositions (A) or (B) or to the mixture (M) of (A) and (B).

There is also no color shift that is visible to the untrained eye with this method. The separating force is likewise very good, however somewhat worse than the aforementioned method in which (D) is not included in (A) or (B) or (M), rather, it is applied, preferably sprayed onto the keratinous fibers after application of (M).

A third preferred color-changing method as contemplated herein the polysaccharide composition (D) is applied in a method step after the application, preferably spraying, of the gelling composition (C) on the keratinous fibers treated with the mixture (M) of (A) and (B).

There is no color shift with this method. The separating force is slightly worse than that of the aforementioned first method in which (D) is applied first, then (C), but is still better than thesecond method with the polysaccharide in (A) or (B) or (M).

For the three aforementioned embodiments of the color-changing method preferred as contemplated herein, the weight ratio of polysaccharide composition (D) to mixture (M) of coloring or lightening composition (A) and oxidation composition (B) is preferably in the range of from about 1:20 to about 1:2, preferably in the range of from about 1:10 to about 1:5.

For the three aforementioned embodiments of the color-changing method preferred as contemplated herein, it is also most preferable for the weight ratio of polysaccharide composition (D) to gelling composition (C) to be in the range of from about 0.2:1 to about 2:1, preferably in the range of from about 0.5:1 to about 1.5:1 and is most preferably about 1:1.

For various embodiments of the present color-changing method preferred as contemplated herein, the weight ratio of gelling composition (D) to mixture (M) of coloring or lightening composition (A) and oxidation composition (B) is likewise preferably in the range of from about 1:20 to about 1:2, preferably in the range of from about 1:10 to about 1:5.

For various embodiments of the present color-changing method preferred as contemplated herein, it is also particularly preferred that said method is applied with at least a second coloring or lightening agent (A'), (A"), (A'") etc. instead of (A), wherein compositions (A) and (A'), (A"), (A'") etc. differ from one another in terms of quality and/or quantity, at least with respect to the oxidation dye precursors and/or partially-oxidizing dyes included therein.

For some embodiments of the present color-changing method preferred as contemplated herein, it is also most preferable for the keratin fiber strands not be provided with solid, flat separating aids, more particularly not with foils from solid materials such as aluminum, paper or Styrofoam.

Another subject matter of the present disclosure is a kit for, preferably multi-tonal, color-changing of keratinous fibers, comprising the following components (D) and (C), as well as optionally (A) and optionally (B), which are physically separated from one another:

I. A polysaccharide composition (D), including
d)i. at least one polysaccharide, which can form a gel with calcium ions in an aqueous medium and which is preferably selected from alginic acid, kappa carragheenan, iota carragheenan and pectin, and/or at least one salt of the aforementioned polysaccharides, selected from the alkali metal-, ammonium-, mono-, di- and trialkyl ammonium-, mono-, di- and trialkanolammonium- and magnesium salts, wherein in the case of salts of the kappa carragheenan, the alkali metal salt thereof is selected only from lithium- and sodium salts, mixtures of alginic acids and sodium alginate being most preferred,
d)ii. at least one alkalizing agent, preferably selected from powdery sodium silicates, most particularly powdery sodium meta silicates,
d)iii. optionally at least one polymer including (meth)acrylic acid-, (meth)acrylic acid ester-, (meth)acrylamide- and/or 2-acrylamido-2-methylpropansulfonic acid monomers, which preferably has no monomers and which can be substituted with ethoxylated, $C_6$-$C_{24}$-alkyl- or $C_6$-$C_{24}$-alkenyl groups;

II. a gelling composition (C'), including
c)i. at least one salt of a polyvalent metal ion selected from calcium-, strontium-, barium- and aluminum salts having a water solubility at about 20° C. of at least about 500 mg/l, and also if the polysaccharide, which forms a gel with calcium ions, comprises kappa carragheenan or a salt thereof, at least one salt selected from potassium-, calcium-, strontium-, barium- and aluminum salts having a water solubility at about 20° C. of at least about 500 mg/l;
c)ii. optionally at least one cation polymer, which is preferably selected from cationized guar ethers.

III. optionally a coloring or lightening composition (A), including
a)i at least one alkalizing agent,
a)ii optionally at least one consistency enhancer and
a)iii optionally at least one solvent, selected from water, one or more mono- or polyvalent alcohols having from about 2 to about 9 carbon atoms, as well as mixtures of said solvents, and
a)iv optionally at least one oxidation dye precursor and/or at least one partially-oxidizing hair dye, wherein the coloring or lightening composition (A), insofar as, relative to its weight, it includes more than about 7 wt. % water, has a pH value in the range of from about 6.0 to about 11.5, measured at about 20° C. and, insofar as the composition (A), relative to its weight, includes from about 0 to about 7 wt. % water, its 30 wt. % dispersion in water has a pH value in the range of from about 6.0 to about 12.0, preferably from about 7.5 to about 11.5, more preferably from about 8 to about 11.0, in each case measured at about 20° C.;

IV. optionally an oxidant composition (B), including
b)i. from about 1 to about 18 wt. % hydrogen peroxide, relative to the weight of the composition (B), and
b)ii. water,
b)iii. wherein the oxidant composition (B) has a pH value in the range from of from about 2.5 to about 6.5, preferably in the range from about 3 to about 5.5, more particularly in the range from about 3.5 to about 5.0, in each case measured at about 20° C.

For kits as contemplated herein, the statements made above on the color-changing method as contemplated herein apply mutatis mutandis.

Preferred kits as contemplated herein have the advantage that the essential ingredients of the compositions (C) and (D) can be commercialized in a space- and packaging-saving manner, for example is sachets, which preferably have a vapor-impermeable layer. For example, the hairdresser can produce the compositions (C) and (D) themselves simply by mixing the compositions (C') and (D') with water and/or an oily hair care composition. Preferably, the kit also comprises instructions for use for applying the preferred color-changing method as contemplated herein.

Another subject matter of the present disclosure is the use of at least one polysaccharide salt, selected from calcium alginate, potassium kappa carragheenat, calcium kappa carragheenat, calcium iota carragheenat, calcium pectinate, aluminum alginate, aluminum kappa carragheenat, aluminum iota carragheenat, aluminum pectinate, strontium alginate, strontium kappa carragheenat, strontium iota carragheenat, strontium pectinate, barium alginate, barium kappa carragheenat, barium iota carragheenat, barium pectinate, as well as mixtures of said polysaccharide salts, for coating keratinous fiber sections or keratinous fiber strands in a method for, preferably multi-tonal, color-changing of keratinous fibers, wherein the color-changing method is preferably a method according to claim 1.

For this use and preferred embodiments as contemplated herein, the statements made above on the preferred color-changing method kits as contemplated herein apply mutatis mutandis.

Test Results

TABLE 1

Lightening or coloring cream (A-1), all quantity specifications in wt. %

| | Coloring cream 1.1 | Coloring cream 1.2 | Lightening cream 1.3 | Lightening cream 1.4 |
|---|---|---|---|---|
| Cetearyl Alcohol | 15.0 | 15.0 | 15.0 | 15.0 |
| Ammonium Hydroxide | 6.3 | 6.3 | 6.3 | 6.3 |
| Glyceryl Stearate | 3.5 | 3.5 | 3.5 | 3.5 |
| Ceteareth-20 | 3.0 | 3.0 | 3.0 | 3.0 |
| Octyldodecanol | 4 | 4 | 4 | 4 |
| Sodium Laureth Sulfate | 1.2 | 1.2 | 1.2 | 1.2 |
| Glycerol | 1.5 | 1.5 | 1.5 | 1.5 |
| Sodium Laureth Sulfate | 0.7 | 0.7 | 0.7 | 0.7 |
| Oleic Acid | 0.4 | 0.4 | 0.4 | 0.4 |
| Perfume (Fragrance) | 0.3 | 0.3 | 0.3 | 0.3 |

TABLE 1-continued

Lightening or coloring cream (A-1),
all quantity specifications in wt. %

|  | Coloring cream 1.1 | Coloring cream 1.2 | Lightening cream 1.3 | Lightening cream 1.4 |
|---|---|---|---|---|
| Potassium Stearate | 0.3 | 0.3 | 0.3 | 0.3 |
| Tetrasodium EDTA | 0.17 | 0.17 | 0.17 | 0.17 |
| Carbomer | 0.2 | 0.2 | 0.2 | 0.2 |
| Polyquaternium-39 | 0.1 | 0.1 | 0.1 | 0.1 |
| Sodium Sulfite | 0.1 | 0.1 | 0.1 | 0.1 |
| Potassium Hydroxide | 0.08 | 0.08 | 0.08 | 0.08 |
| Ascorbic Acid | 0.05 | 0.05 | 0.05 | 0.05 |
| Linoleamidopropyl PG-Dimonium Chloride Phosphate | 0.03 | 0.03 | 0.03 | 0.03 |
| 1-hydroxyethyl 4,5-Diamino Pyrazole Sulfate | 1.5 | 1.5 | — | — |
| 4-amino-3-methylphenol | 0.18 | 0.18 | — | — |
| 4-amino-2-hydroxytoluol | 0.3 | 0.3 | — | — |
| m-aminophenol | 0.6 | 0.6 | — | — |
| Citric Acid | 0.002 | 0.002 | 0.002 | 0.002 |
| Alginic acid | — | 1.25 | — | 1.25 |
| Sodium alginate | — | 1.25 | — | 1.25 |
| Aqua (Water, Eau) | ad 100 | ad 100 | ad 100 | ad 100 |

TABLE 2

Oxidation composition (B), all quantity specifications in wt. %

| Paraffinum liquidum | 17.0 |
|---|---|
| Hydrogen Peroxide | 6.0 |
| Cetearyl Alcohol | 4.0 |
| PEG-40 Castor Oil | 0.8 |
| Sodium Laureth Sulfate | 0.5 |
| Etidronic Acid, | 0.2 |
| Potassium Hydroxide | 0.12 |
| Disodium pyrophosphate | 0.1 |
| 2,6-Dicarboxypyridine | 0.1 |
| Sodium Benzoate | 0.01 |
| Aqua (Water, Eau) | ad 100 |

Spray Application of Film-Forming Polysaccharide

Dye cream 1.1 or lightening cream 1.3 according to Table 1 were mixed in a 1:1 weight ratio with the: oxidation composition (B) according to table 2.

Half of the hair of a human-hair wig was colored strand-by-strand, alternating between coloring cream and bleaching cream. After the 1:1 mixture of coloring cream 1.1+B was applied to each strand, a hydrous solution (D) including 1.25 wt. % alginic acid, 1.25 wt. % sodium alginate, sodium metasilicate up to pH 8.5 and 1 wt. % C10-C13 isoparaffin and water ad 100 wt. %

Then a hydrous solution (C) including 1 wt. % calcium chloride, 0.5 wt. % hydroxypropylguarhydroxypropyl trimonium chloride, citric acid up to pH 4 and water ad 100 wt. % was applied by spraying. The strands were perceptibly firmer.

Then, after application of a 1:1 mixture of lightening cream 1.3+B on an adjacent strand, the aforementioned hydrous solution (D) was sprayed and then the hydrous solution (C) was sprayed. The strands became perceptibly firmer.

During all spraying process, the half of the head treated with the mixture of 1.2+B and 1.4+B was covered with a towel in order to prevent falsification of the comparison test.

The other half of the wig was colored accordingly, alternating strand-by-strand between coloring cream 1.2+B and 1.4+B with bleaching cream. Only the aforementioned hydrous solution (C) was sprayed on the strands. In the process, the strands became perceptibly firmer.

After the entire head of hair was colored, the strands were carefully pressed down on the head by hand. After an application time of 45 minutes with an environmental temperature of 20° C. without the introduction of additional heat, the hair was washed with water and a shampoo, treated with a conditioner and washed again, then dried with a towel and a hairdryer.

The colorimetric evaluation showed no color shift for the colorations without polysaccharide calcium gel.

The strands with 1.1 and 1.3 sprayed with D and C had a better separating force, which means less coloring/lighting agent contamination between adjacent different colored and/or decolorized strands than for the method with the compositions 1.2 and 1.4.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method for color-changing keratinous fibers, said method comprising the steps of:
   a. preparing a coloring or lightening composition (A), comprising
      a)i. at least one alkalizing agent,
      a)ii. optionally at least one consistency enhancer, and
      a)iii. optionally at least one solvent, wherein the at least one solvent is selected from water, monovalent or polyvalent alcohols having from 2 to 9 carbon atoms, and polyethylene glycols having from 2 to 20 ethylene glycol units, and
      a)iv. optionally at least one oxidation dye precursor and/or at least one partially-oxidizing hair dye,
      a)v. wherein when the coloring or lightening composition (A), relative to its weight, comprises more than about 7 wt. % water, it has a pH value of from about 6.0 to about 11.5, measured at 20° C. and, wherein, when the composition (A), relative to its weight, comprises from about 0 to about 7 wt. % water, its 30 wt. % dispersion in water has a pH value of from about 6.0 to about 12.0, measured at 20° C.;
   b. preparing an oxidant composition (B), comprising
      b)i. from about 1 to about 18 wt. % hydrogen peroxide, relative to the weight of the composition (B), and
      b)ii. water,
      b)iii. wherein the oxidant composition (B) has a pH value from about 2.5 to about 6.5,
   c. preparing a gelling composition (C), comprising
      c)i. from about 0.1 to about 3 wt. %, relative to the weight of the composition (C), of at least one salt of a multivalent metal ion, selected from calcium-, strontium-, barium- and aluminum salts having a water solubility at 20° C. of at least about 500 mg/l,
      c)ii. from about 50 to about 99 wt. % water, relative to the weight of the composition (C), c)iii. optionally at least one cation polymer selected from cationized guar ethers, c)iv. wherein the gelling composition (C) has a pH value from about 4 to about 12, measured at about 20° C.;

the gelling composition (C) optionally being produced in-situ or from about 0.01 to about 24 hours before said method is applied by mixing a solid, gelling composition (C'), comprising the at least one salt c)i in powder form and optionally at least one cation polymer, which is selected from cationized guar ethers, in powder form, with water c) iii, then, from about 1 to about 600 seconds thereafter, d. producing a mixture (M) of (A) and (B), having a pH value of from about 6.0 to about 11, measured at about 20° C.; after from about 1 to about 600 seconds;

e. applying at least one partial quantity of (M) on at least one keratin fiber section to be colored and/or lightened;

from about 1 to about 600 seconds thereafter f. applying the gelling composition (C) on the keratinous fiber section(s) treated with (M);

g. repeating steps e. and f. as many times as desired, h. leaving the gelling composition (C) on the keratinous fibers for a time of from about 0.1 to about 60 minutes, and then rinsing the keratinous fibers with water and, if required, with a cleaning agent, post-treating the fibers with a conditioning agent and then drying, if required, wherein said method comprises applying at least one polysaccharide or a salt of a polysaccharide which can form a gel with calcium ions in an aqueous medium, wherein the salt of a polysaccharide is selected from the alkali metal-, ammonium-, mono-, di- and trialkyl ammonium-, mono-, di- and trialkanolammonium-, and magnesium salts, wherein in the case of salts of the kappa carragheenan, the alkali metal salt thereof is selected from lithium- and sodium salts, wherein these polysaccharides are not included in the gelling composition (C), and wherein the polysaccharides are included in (A), in (B), or in both (A) and (B), or wherein the polysaccharides are applied as a hydrous solution after the mixture of (A) and (B) and before applying the gelling composition (C); or wherein the polysaccharides are applied as a hydrous solution after the gelling composition (C).

2. The method according to claim 1 wherein the at least one polysaccharide and/or the at least one salt of the aforementioned polysaccharides is included in the coloring or lightening composition (A), in a total amount of from about 0.1 about 5 wt. %, relative to the weight of the composition (A).

3. The method according to claim 1 wherein the at least one polysaccharide and/or at least one salt of the aforementioned polysaccharides is included in the oxidation composition (B), in a total amount of from about 0.1 to about 5 wt. %, relative to the weight of the composition (B).

4. The method according to claim 1 wherein the at least one polysaccharide or salt of a polysaccharide is prepared in the form of a polysaccharide composition (D), comprising d)i. the at least one polysaccharide or salt of a polysaccharide, d)ii. from about 50 to about 99.9 wt. % water, relative to the weight of the composition (D), d)iii. optionally at least one alkalizing agent, which is selected from powdery sodium silicates, d)iv. optionally at least one polymer, comprising (meth) acrylic acid-, (meth)acrylamide- and/or 2-acrylamido-2-methylpropane sulfonic acid monomers, in a total quantity of from about 0.05 to about 3 wt. %, relative to the weight of the composition (D), d)v. optionally at least one oil in a total quantity of from about 0.1 to about 10 wt. %, relative to the weight of the polysaccharide composition (D), wherein the polysaccharide composition (D), in one method step, is applied after application step e and before application of the gelling composition (C) onto the keratinous fiber(s) treated with the mixture (M) of (A) and (B), or before application step e, is added to composition (A) or (B) or to the mixture (M) of (A) and (B), or after application of the gelling composition (C) onto the keratinous fiber(s) treated with the mixture (M) of (A) and (B).

5. The method according to claim 1, wherein the weight ratio of coloring or lightening composition (A) to oxidant composition (B) is of from about 1:10 to about 4:1.

6. The method according to claim 4, wherein the weight ratio of polysaccharide composition (D) to mixture (M) of coloring or lightening composition (A) and oxidant composition (B) is of from about 1:20 to about 1:2.

7. The method according to claim 1, wherein the weight ratio of gelling composition (C) to mixture (M) of coloring or lightening composition (A) and oxidant composition (B) is of from about 1:20 to about 1:2.

8. The method according to claim 4, wherein the weight ratio of polysaccharide composition (D) to gelling composition (C) is of from about 0.2:1 to about 2:1.

9. The method according to claim 1, wherein said method is applied with at least a second coloring or lightening composition (A'), wherein compositions (A) and (A') differ from one another with respect to the partially-oxidizing hair dyes included therein.

10. The method according to claim 1, wherein the keratinous fiber strands are not provided with solid, flat separating aids.

11. A kit for multi-tonal color-changing of keratinous fibers, comprising the following components (D) and (C), optionally (A) and optionally (B), which are physically separated from one another wherein:

I. a polysaccharide composition (D), comprises d)i. at least one polysaccharide, which can form a gel with calcium ions in an aqueous medium and which is selected from alginic acid, kappa carragheenan, iota carragheenan and pectin, and/or at least one salt of the aforementioned polysaccharides, selected from the alkali metal-, ammonium-, mono-, di- and trialkyl ammonium-, mono-, di- and trialkanolammonium- and magnesium salts, wherein in the case of salts of the kappa carragheenan, the alkali metal salt thereof is selected from lithium- and sodium salts, d)ii. at least one alkalizing agent, selected from powdery sodium silicates, d)iii. optionally at least one polymer comprising (meth) acrylic acid-, (meth)acrylic acid ester-, (meth)acrylamide- and/or 2-acrylamido-2-methylpropansulfonic acid monomers;

II. a gelling composition (C), comprises c)i. at least one salt of a polyvalent metal ion selected from calcium-, strontium-, barium- and aluminum salts having a water solubility at about 20° C. of at least about 500 mg/l, and also if the polysaccharide, which forms a gel with calcium ions, comprises kappa carragheenan or a salt thereof, at least one salt selected from potassium-, calcium-, strontium-, barium- and aluminum salts having a water solubility at about 20° C. of at least about 500 mg/l;

c)ii. optionally at least one cation polymer, which is selected from cationized guar ethers, III. optionally a coloring or lightening composition (A), comprises a)i at least one alkalizing agent, a)ii optionally at least one consistency enhancer and a)iii optionally at least one solvent, selected from water and one or more mono- or polyvalent alcohols having 2 to 9 carbon atoms and a)iv optionally at least oxidation dye precursor and/or at least one partially-oxidizing hair dye, wherein when the coloring or lightening composition (A), relative to its weight, it comprises more than about 7 wt. % water, has a pH value of from about 6.0 to about 11.5, measured at about 20° C. and, wherein, when the composition (A), relative to its weight, comprises from about 0 to about 7 wt. % water, it is an about 30 wt. % dispersion in water and has a pH value of from about 6.0 to about 12.0 measured at about 20° C.; and IV. optionally an oxidant composition (B), comprising b)i. from about 1 to about 18 wt. % hydrogen peroxide, relative to the weight of the composition (B), and b)ii. water, and b)iii. wherein the oxidant composition (B) has a pH value of from about 2.5 to about 6.5, measured at about 20° C.

12. The kit according to claim 11, wherein the at least one polymer of d)iii, is selected from cross-linked homopolymers of acrylic acid, cross-linked homopolymers of 2-acrylamido-2-methylpropansulfonic acid, cross-linked copolymers comprising acrylic acid—and 2-acrylamido-2-methylpropansulfonic acid units, cross-linked copolymers comprising 2-methyl-2[(1-oxo-2-propenyl)amino]-1-propansulfonic acid units and hydroxyethylacrylate units, cross-linked copolymers comprising acrylamide- and 2-acrylamido-2-methylpropansulfonic acid units, cross-linked copolymers comprising methacrylic acid units and C1-C4-alkyl acrylate units, and cross-linked copolymers comprising acrylic acid units and C1-C4-alkylmethacrylate units.

13. The method according to claim 1 wherein the coloring composition (A) comprises at least one oxidation dye precursor selected from 4,5-diamino-1-(2-hydroxyethyl)pyrazol, 4-amino-3-methylphenol, 4-amino-2-hydroxytoluene and m-aminophenol.

14. The method according to claim 1 wherein the 30 wt. % dispersion in water has a pH value of from about 8 to about 11, measured at about 20° C.

15. The method according to claim 1 wherein the oxidant composition (B) has a pH value of from about 3.5 to about 5.0.

16. The method according to claim 1 wherein c)i is present in an amount of about 0.4 to about 1 wt. % relative to the weight of the composition (C).

17. The method according to claim 1 wherein the gelling composition (C) has a pH value from about 6.5 to about 8, measured at about 20° C.

18. The method according to claim 1 wherein the step of leaving the gelling composition (C) on the keratinous fibers is for a time of from about 30 to about 45 minutes.

19. The method according to claim 1 wherein the step of leaving the gelling composition (C) on the keratinous fibers is for a time of from about 10 to about 45 minutes.

20. The method according to claim 1 wherein the 30 wt. % dispersion in water has a pH value of from about 8 to about 11, measured at about 20° C., wherein the oxidant composition (B) has a pH value of from about 3.5 to about 5.0, wherein c)i is present in an amount of about 0.4 to about 1 wt. % relative to the weight of the composition (C), wherein the gelling composition (C) has a pH value from about 6.5 to about 8, measured at about 20° C., and wherein the step of leaving the gelling composition (C) on the keratinous fibers is for a time of from about 30 to about 45 minutes.

* * * * *